US011000056B2

(12) United States Patent
Dueva-Koganov et al.

(10) Patent No.: US 11,000,056 B2
(45) Date of Patent: May 11, 2021

(54) **BIOACTIVE SERUM FRACTION FROM ACHACHAIRU (*GARCINIA HUMILIS*) WHICH IS FREE OF BENZOPHENONE AND PROTEINS**

(71) Applicant: ISP Investments LLC, Wilmington, DE (US)

(72) Inventors: Olga Dueva-Koganov, White Plains, NY (US); Michael Koganov, White Plains, NY (US); Paul Recht, Pleasantville, NY (US); Artyom Duev, White Plains, NY (US); Li Zhang, Princeton, NJ (US); Steven Micceri, Milford, CT (US); Robert Turner, Peekskill, NY (US)

(73) Assignee: ISP Investments LLC, Wilmington, DE (US)

( * ) Notice: Subject to any disclaimer, the term of this patent is extended or adjusted under 35 U.S.C. 154(b) by 218 days.

(21) Appl. No.: 16/060,284

(22) PCT Filed: Dec. 8, 2016

(86) PCT No.: PCT/US2016/065581
§ 371 (c)(1),
(2) Date: Jun. 7, 2018

(87) PCT Pub. No.: WO2017/100430
PCT Pub. Date: Jun. 15, 2017

(65) Prior Publication Data
US 2020/0046006 A1    Feb. 13, 2020

Related U.S. Application Data

(60) Provisional application No. 62/264,401, filed on Dec. 8, 2015.

(51) Int. Cl.
*A61K 36/38* (2006.01)
*A23L 33/105* (2016.01)
*A23L 2/02* (2006.01)

(52) U.S. Cl.
CPC ............... *A23L 33/105* (2016.08); *A23L 2/02* (2013.01); *A61K 36/38* (2013.01)

(58) Field of Classification Search
None
See application file for complete search history.

(56) References Cited

U.S. PATENT DOCUMENTS

| | | | | |
|---|---|---|---|---|
| 10,172,787 B2 * | 1/2019 | Osborne | .................. | A61K 8/44 |
| 10,182,981 B2 * | 1/2019 | Osborne | ................ | A61K 8/368 |
| 10,335,363 B2 * | 7/2019 | Osborne | ................ | A61K 8/368 |
| 10,369,097 B1 * | 8/2019 | Osborne | .................. | A61K 8/36 |
| 10,537,515 B2 * | 1/2020 | Osborne | .................. | A61Q 5/02 |

FOREIGN PATENT DOCUMENTS

WO    WO 2014/140054 A1    9/2014

OTHER PUBLICATIONS

Shu, Y. et al. Microwave Assisted Extraction of Ginsenosides from Ginseng Root. Microchemical J 74:131-139 2003. (Year: 2003).*
Niero R. et al. Gastroprotective Effects of Extracts and Guttiferone A Isolated from Garcinia achachairu . . . Naunyn-Schnniedeberg's Archives Pharmacology 385(11)1103-1109, 2012. (Year: 2012).*
Manhabosco M. et al. Phytochemical Analysis and Antinociceptive Properties of the Seeds of Garcinia achachairu. Archives Pharmacal Research 35(4)623-631, Apr. 2012. (Year: 2012).*
International Search Report of PCT Application No. PCT/US2016/065581 published on Jun. 15, 2017.
Patil et al., Garcinia: Bioactive compounds and health benefits, Introduction to Functional Food Science, Jan. 2013 [retrieved on Jan. 11, 2017]. Retrieved from the Internet: <URL: https://www.researchgate.net/profile/Mahesh_Patil13/publication/273756138_Garcinia_Bioactive_compounds_and_health_benefit_in_Functional_Food_Science/links/5673c19508ae04d9b09bdb55.pdf>. pp. 110-125.
Pimentel, Caracterizacao Qualitativa de Frutos de Achachairu (*Garcinia humilis* (Vahl) C.D. Adam) Cultivados Em Moreno-PE, Recife-PE, 2012 [retrieved on Mar. 16, 2017]. Retrieved from the Internet: <URL: http://www.tede2.ufrpe.br:8080/tede/bitsream/tede2/5091/2/Maria% 20Rafaella%20da%20Fonseca%20Pimentel.pdf>.

* cited by examiner

*Primary Examiner* — Ralph J Gitomer
(74) *Attorney, Agent, or Firm* — William J. Davis; Nathalie Tietcheu

(57) ABSTRACT

The present invention provides bioactive serum fractions and bioactive extracts derived from an Achachairu (*Garcinia humilis*) plant. The bioactive serum fractions and bioactive extracts are free of or substantially free of benzophenone and/or free of or substantially free of proteins. The present invention also provides products comprising the bioactive serum fractions and/or bioactive extracts. The present invention further provides methods of making the bioactive serum fractions and/or bioactive extracts.

4 Claims, 11 Drawing Sheets

BIOACTIVE SERUM FRACTION FROM ACHACHAIRU (GARCINIA HUMILIS) WHICH IS FREE OF BENZOPHENONE AND PROTEINS

CROSS REFERENCE TO RELATED APPLICATIONS

This application is a U.S. National Phase filing under 35 U.S.C. § 371 of International Application No. PCT/US2017/013676, filed Jan. 16, 2017, and published as WO 2017/124075 A1 on Jul. 20, 2017 which claims benefit of priority from U.S. Provisional Patent Application Ser. No. 62/279,242, filed Jan. 15, 2017. The entire contents of each of the prior applications are incorporated herein by reference in their entirety.

FIELD OF THE INVENTION

The present invention relates to bioactive compositions (including, for example, bioactive serum fractions and bioactive extracts) derived from Achachairu (*Garcinia humilis*) whole fruit, a particular part of fruit, leaves, or any combination of parts of fruit and/or leaves. Further, the bioactive serum fractions and bioactive extracts have anti-inflammatory and/or anti-irritant and/or anti-aging activities.

BACKGROUND OF THE INVENTION

The Clusiaceae (or Guttiferae) family is distributed mainly in tropical regions and comprises about 40 genera and 1,200 species, the genus *Garcinia* (ex-Rheedia) being the most numerous, with about 400 species widely distributed in tropical Brazil, Polynesia, New Caledonia, Africa, and Asia (Ampofo S A, Waterman P G (1986) Xanthones and neoflavonoids from two Asian species of *Calophyllum*. Phytochemistry 25: 2617-2620).

Achachairu (*Garcinia humilis*), also known as Achacha, belongs to the Clusiaceae (or Guttiferae) family, the genus *Garcinia*; it is widely distributed in the region of Santa Cruz, Bolivia and is well-adapted in Brazil, Australia and Puerto Rico. This plant is used in Bolivian folk medicine for its healing, digestive, and laxative properties (Barbosa W, Artiole F A (2007) A fruta achachairu. infobibos.com/Artigos/2007_1/achachairu/index.htm). In Brazil, it is popularly known as "achachairu" and is used in folk medicine to treat rheumatism, inflammation, pain and gastric disorders (Alves T M A, Silva A F, Brandão M, Grandi T S M, Smânia E F et al. (2000) Biological Screening of Brazilian Medicinal Plants. Mem Inst Oswaldo Cruz 95: 367-373 and Barbosa W, Chagas E A, Martins L, Pio R, Tucci M L et al. (2008) Germinação de sementes e desenvolvimento inicial de plântulas de achachairu. Rev Bras Frutic 30: 263-266).

The antibacterial activity of four species from the Brazilian flora (*Garcinia achachairu*, *Macromphonia velame*, *Rubus niveus* and *Pilea microphylla*) against *Bacillus subtilis*, *Staphylococcus aureus* and *S. saprophyticus* (Grampos. bacteria), *Escherichia coli* (Gram-neg. bacterium) and *Candida albicans* (yeast) was investigated. The extracts of *R. niveus* and *M. velame* showed promising antibacterial activity with MICs, ranging from 1000 to 125 µg/mL. Bio-guided fractionation of *M. velame* yielded four compounds, with the highest inhibition being obsd. for compd. 3, with a MIC of 125 µg/mL against *S. aureus* (Melim, Carla; Guimaraes, Karoliny; Martin-Quintal, Zhelmy; Alves, Aurea Damaceno; Tabajara de Oliveira Martins, Domingos; Monache, Franco Delle; Filho, Valdir Cechinel; Cruz, Alexandre Bella; Niero, Rivaldo. Antimicrobial activity of extracts and fractions from aerial parts of selected plants (*Garcinia achachairu*, *Macromphonia velame*, *Rubus niveus* and *Pilea microphylla*) against some pathogenic microorganisms. Nat Prod Commun. 2013 November; 8(11):1567-9). This particular reference suggests that the antimicrobial activity of *Garcinia achachairu* extract was not as promising as activity of the extracts of *R. niveus* and *M. velame*.

Phytochemical characterization of seed extract of *G. achachairu* reveals the presence of benzophenones, xanthones and bioflavonoids, such as guttiferone N, garcinol, isogarcinol, guttiferone M, camboginol, xanthochymol and guttiferone A, with benzophenone guttiferone A as the major compound (Molin M M D, Silva S, Alves D R, Quintão N L M, Monache F D et al. (2012) Phytochemical analysis and antinociceptive properties of *Garcinia achachairu* Rusby (Clusiaceae) seeds. Arch Pharm Res 35: 623-631 and Marques E S, Silva S, Niero R, Andrade S F, Rosa P C P et al. (2012) Genotoxicity assessment of *Garcinia achachairu* Rusby (Clusiaceae) extract in mammalian cells in vivo. J Ethnopharmacol 142: 362-366).

Benzophenones are known to exhibit various biological activities, such as cytotoxic, antimicrobial, antiviral and antioxidant (Acuña U M, Jancovski N, Kennelly E J (2009) Polyisoprenylated benzophenones from Clusiaceae: potential drugs and lead compounds. Curr Top Med Chem 9: 1560-1580). Benzophenones are major intermediates in the biosynthetic pathway of xanthones, and are rarely reported to occur outside the Clusiaceae family (Beerhues L (1996) Benzophenone synthase from cultured cells of *Centaurium erythraea*. FEBS Lett 383: 264-266). Benzophenones are non-polar phenolic compounds, which show increased hydrophobicity as the number of attached prenyl functional groups increases. Potent biological properties of benzophenones have been the subject of several studies (Acuña U M, Jancovski N, Kennelly E J (2009) Polyisoprenylated benzophenones from Clusiaceae: potential drugs and lead compounds. Curr Top Med Chem 9: 1560-1580).

Niero et al. reported that extracts obtained from *G. achachairu*, and its major benzophenone compound Guttiferone A, produce gastroprotective effects against induced gastric lesions in mice (Niero R, Dal Molin M M, Silva S, Damian N S, Maia L O et al. (2012) Gastroprotective effects of extracts and guttiferone A isolated from *Garcinia achachairu* Rusby (Clusiaceae) against experimentally induced gastric lesions in mice. NaunynSchmiedebergs Arch. Pharmacologist 385(11): 1103-1109).

The same research group reported that the seed extract of *G. achachairu* and the compound Guttiferone A present antinociceptive effects (Molin M M D, Silva S, Alves D R, Quintão NLM, Monache F D et al. (2012) Phytochemical analysis analysis and antinociceptive properties of *Garcinia achachairu* Rusby (Clusiaceae) seeds. Arch Pharm Res 35: 623-631).

Thus, benzophenones from natural sources and those of synthetic analogues present potent biological properties, and Guttiferone A could represent a promising medicinal natural compound with analgesic and gastroprotective profiles.

The molecular structure of Guttiferone A isolated from *Garcinia achachairu* is presented below:

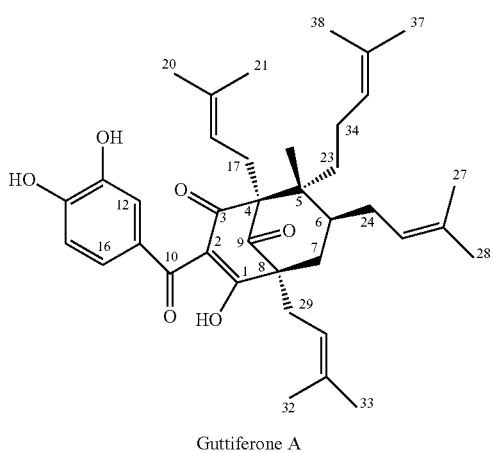 [SMILES: CC(C)=CCC[C@]1(C)[C@@H](CC=C(C)C)C[C@]2(CC=C(C)C)C(=O)[C@@]1(CC=C(C)C)C(=O)C(C(=O)c1ccc(O)c(O)c1)=C2O]

Guttiferone A

The genetic toxicity of Guttiferone A from seeds of *Garcinia achachairu* was investigated in terms of DNA damage in different cells of Swiss albino mice using the comet assay. Clastogenic/aneugenic effects Guttiferone A were investigated in bone marrow cells in vivo by the micronucleus test. Since the Guttiferone A is not used by humans yet, the treatment regimen and the administration method used in this study was considered the most suitable for humans, and the tested doses were chosen on the basis of its gastroprotective effects previously evaluated in rodents by Niero et al. Cytotoxicity was assessed by scoring polychromatic (PCE) and normochromatic (NCE) erythrocytes ratio. Guttiferone A was administered by oral gavage at doses of 15, 30 and 60 mg/kg. The PCE/NCE ratio indicated no cytotoxicity. The results showed that Guttiferone A produced genotoxic effects in leukocytes, liver, bone marrow, brain and testicle cells and clastogenic/aneugenic effects in bone marrow erythrocytes of mice.

Since it was discovered that Guttiferone A is harmful to the genetic material, a caution in its use by humans was suggested (Terrazas P M, de Souza Marques E, Mariano L N B, Cechinel-Filho V, Niero R, Andrade S F, et al. (2013) Benzophenone guttiferone A from *Garcinia achachairu* Rusby (Clusiaceae) Presents Genotoxic Effects in Different Cells of Mice. PLoS ONE 8(11): e76485).

Another naturally occurring benzophenone that is found in some flowering plants is Benzophenone-3 (BP-3, AKA Oxybenzone). According to the CDC (U.S. Centers for Disease Control and Prevention), BP-3 absorbs and scatters the sun's harmful ultraviolet (UV) rays. For this reason, it is produced for use as sunscreen in lotions, conditioners, and cosmetics. BP-3 also is used in plastic products to block and prevent UV rays from altering the plastic and the contents inside. Once applied, a small amount of BP-3 passes through the skin into the body. BP-3 has been shown to cause weak hormonal activity in laboratory animals. More research is needed to assess the human health effects of exposure to BP-3. CDC scientists found BP-3 in the urine of nearly all of the people tested, indicating widespread exposure to BP-3 in the U.S. population. Finding a measurable amount of BP-3 in urine does not imply that levels of BP-3 cause an adverse health effect. Biomonitoring studies on levels of BP-3 provide physicians and public health officials with reference values so they can determine whether people have been exposed to higher levels of BP-3 than are found in the general population. Biomonitoring data can also help scientists plan and conduct research on exposure and health effects (www.cdc.gov/biomonitoring/Benzophenone-3_FactSheet.html).

BP-3 is a lipophilic, photostable, and bioaccumulative compound, and can be rapidly absorbed via oral and dermal routes. An increasing number of in vitro studies have indicated the endocrine disrupting capacity of BP-3. Based on a receptor binding assay, BP-3 has shown strong anti-androgenic and weak estrogenic activities but at the same time BP-3 displays anti-estrogenic activity as well (Kim S, Choi K., Occurrences, toxicities, and ecological risks of benzophenone-3, a common component of organic sunscreen products: a mini-review. Environ Int. 2014 September, 70:143-57).

Proteins including those in bioactive ingredients for topical applications can cause protein contact dermatitis in sensitive individuals. Shortly after contact with the causative proteinaceous material, such individuals can experience symptoms such as acute urticarial or vesicular eruption on the skin, often accompanied by pruritus, burning, and/or stinging (V. Janssens, et al., "Protein contact dermatitis: myth or reality?", British Journal of Dermatology 1995; 132: 1-6).

The above references indicate that both groups of compounds, benzophenones and proteins, could be considered as unwanted compounds of concern—if they are present in certain plant derived bioactive compositions (ingredients) at certain concentrations.

Achachairu (*Garcinia humilis*) is a potential source of bioactive compositions (ingredients), especially if certain unwanted components of concern (e.g., benzophenones, proteins) are removed or their concentrations are substantially reduced in these compositions.

Thus, it is highly desirable to obtain bioactive compositions from Achachairu (*Garcinia humilis*) that contain as little benzophenones and as little protein as possible.

A significant task exists in simultaneously removing or substantially reducing the concentrations of benzophenones and protein in the bioactive compositions obtained from Achachairu (*Garcinia humilis*).

In addition, it is feasible to assume that certain parts of Achachairu (*Garcinia humilis*) fruit could be used to obtain natural benzophenone-enriched bioactive compositions, suitable for certain applications.

The present invention is directed toward addressing these and other deficiencies in the prior art.

SUMMARY OF THE INVENTION

The present invention relates to bioactive compositions (ingredients) derived from Achachairu (*Garcinia humilis*) whole fruit, a particular part of the fruit, leaves, or any combination of parts of the fruit and/or leaves. More particularly, in certain embodiments, the bioactive compositions (ingredients) of the present invention are free of or substantially free of benzophenones (e.g. Guttiferone A) and protein. Further, the bioactive compositions (ingredients) have anti-inflammatory and/or anti-aging and/or anti-irritant activities. The present invention also relates to a method for isolating bioactive compositions (ingredients) derived from Achachairu (*Garcinia humilis*) whole fruit, a particular part of fruit, leaves, or any combination of parts of fruit and/or leaves that are free or substantially free of benzophenones (e.g., Guttiferone A) and proteins. The present invention also relates to a method for preparing bioactive compositions (ingredients) derived from Achachairu (*Garcinia humilis*) whole fruit, a particular part of fruit, leaves, or any combination of parts of fruit and/or leaves that are stabilized and are either free of or substantially free of benzophenones (e.g., Guttiferone A) and proteins.

In certain embodiments of the present invention, a particular part of the Achachairu (*Garcinia humilis*) fruit could be used to obtain natural benzophenone-enriched bioactive compositions (ingredients) by using the same method described in the present invention.

BRIEF DESCRIPTION OF THE DRAWINGS

For the purpose of illustrating aspects of the present invention, there are depicted in the drawings certain embodiments of the invention. It is believed that the present invention will be better understood from the following description taken in conjunction with the accompanying drawings. The referenced drawings are not to be construed as limiting the scope of present invention.

FIG. 3A illustrates absorbance spectra of a wavelength range of 200-400 nm. FIG. 3B illustrates absorbance spectra of a wavelength range of 400-1000 nm.

FIG. 4A illustrates absorbance spectra of a wavelength range of 200-400 nm. FIG. 4B illustrates absorbance spectra of a wavelength range of 400-1000 nm.

DETAILED DESCRIPTION OF THE INVENTION

Figure 1:
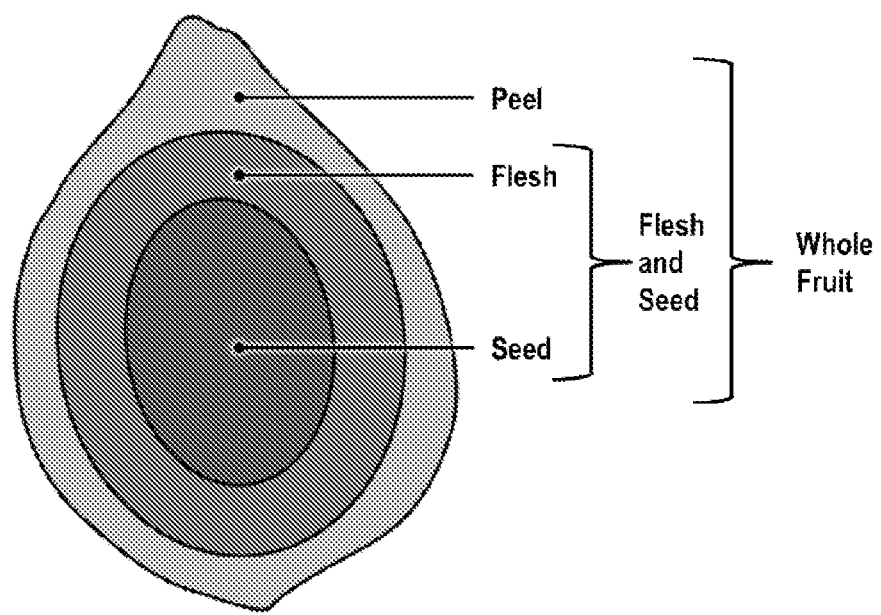
FIG. 1 is a schematic of a cross-sectional view of the fruit of an Achachairu (*Garcinia humilis*) plant.

It has now been discovered that the Achachairu (*Garcinia humilis*) plant, also commonly referred to as Achacha, especially bioactive serum fractions and bioactive extracts obtained from Achachairu, possess properties that may be beneficial for various personal care, nutraceutical, and functional food applications. In particular, bioactive Achachairu fruit serum fractions and extracts exhibit surprising properties related to anti-oxidation, anti-inflammation, anti-aging, and anti-irritant activities.

Therefore, in certain aspects, the present invention provides bioactive serum fractions and bioactive extracts derived from an Achachairu (*Garcinia humilis*) plant. In certain embodiments, the bioactive serum fractions and bioactive extracts are free of or substantially free of benzophenone and/or free of or substantially free of proteins. The present invention also provides products and compositions comprising the bioactive serum fractions and/or bioactive extracts. The present invention further provides methods of making the bioactive serum fractions and/or bioactive extracts.

The products and compositions of the present invention can comprise, consist essentially of, or consist of, the essential components (e.g., the bioactive serum fractions and bioactive extracts derived from an Achachairu (*Garcinia humilis*) plant) as well as optional ingredients described herein. As used herein, "consisting essentially of" means that the composition or component may include additional ingredients, but only if the additional ingredients do not materially alter the basic and novel characteristics of the claimed compositions or methods.

Definitions

"Apply" or "application", as used in reference to a composition, means to apply or spread the compositions of the present invention onto a mammal skin surface such as the epidermis.

As used herein, the term "cosmetically acceptable" refers to bioactive ingredients, formulations, cosmetically active agents, or inert ingredients that are suitable for use in contact with mammalian tissues (e.g., the skin of humans), including topical applications, without undue toxicity, incompatibility, instability, irritation, allergic response, and the like, commensurate with a reasonable benefit/risk ratio.

"Dermatologically acceptable" means that the compositions or components described are suitable for use in contact with human keratinous tissue without undue toxicity, incompatibility, instability, allergic response, and the like.

"Exogenous solvent" means any solvent placed in contact with the plant material for the purpose of separating compounds from the plant material. It may be a solvent originally present in plant material but added in higher amounts (e.g., in case of water extracts), or a solvent not inherently present in plant material. Plant material herein can include any solid or liquid portion of the Achachairu plant.

"Extract," when referring to Achachairu, means a compound (e.g., one or more phytochemicals) obtained from a portion of Achachairu plant material (e.g., peel, fruit, seed, stem, bark, leaves, roots, and/or a combination of these), which may be fresh, dried, or partially dried, by contacting the plant material(s) with an exogenous solvent and separating the desired material compound from the solvent using a conventional extraction process. Conventional extraction processes for separating a compound from an exogenous solvent are well known in the art.

"Salts" refer to ionic form of a given compound combined with counterions deemed acceptable for a given application (e.g., food, topical, pharmaceutical). Examples include but are not limited to sodium, potassium, calcium, ammonium, manganese, copper, and/or magnesium salts of a given compound.

"Topical" refers to a composition that is intended to be applied to a bodily surface such as skin or hair.

As used herein, the term "topical application" generally refers to techniques relating to directly laying on or spreading the bioactive ingredients of the present invention or formulations containing these bioactive ingredients onto the outer skin using, e.g., by use of the hands or an applicator such as a wipe.

As used herein, the term "acceptable in functional food and beverage products" refers to bioactive ingredients, formulations or inert ingredients that are suitable for internal use without undue toxicity, incompatibility, instability, irritation, allergic response, and the like, commensurate with a reasonable benefit/risk ratio.

Serum Fractions of Achachairu (*Garcinia humilis*)

In one embodiment, suitable Achachairu (*Garcinia humilis*) fruit for use in the present invention were collected in Puerto Rico in 2013-2015.

As shown in FIG. 1, the fruit of the Achachairu (*Garcinia humilis*) plant is comprised of distinct layers and parts. FIG. 1 illustrates a typical structure as shown by a section passing through a long axis of the fruit. Whole fruit, a particular part of fruit, or any combination of parts of fruit may be used for further processing in accordance with the present invention. However, this is not meant to exclude further distinctions of fruit parts than described here, or leaves that may be retained during harvesting.

As used herein and in the schematic of FIG. 1, the terms "Whole Fruit", "Peel", "Flesh", and "Seed" refer to the Achachairu fruit (Whole Fruit) and its parts (Peel, Flesh, and/or Seed) as further described below. The outermost layer of the whole fruit is the "Peel", which is comparatively thick and tough. The next inward layer is the "Flesh", which is comparatively soft and yielding. The flesh surrounds a comparatively large "Seed". Especially large fruit may have more than one seed. In certain instances, while these terms may be used without initial capitalization formatting (e.g., whole fruit, peel, flesh, and seed), these terms still maintain the same meaning as referenced above, as one of ordinary skill in the art would understand.

The present invention provides a commercially viable process for removing or substantially reducing the benzophenones (e.g., Guttiferone A) and protein content in bioactive ingredients obtained from Achachairu (*Garcinia humilis*).

As used herein, "substantially free of proteins" means less than 0.15% total protein content determined by hydrolyzed and un-hydrolyzed amino acid analysis conducted on Hitachi L-8900 amino acid analyzer.

As used herein, "substantially free of benzophenones" means less than 0.1% total benzophenones, including Guttiferone A; its content determined by the method described in Dal Molin M M, Silva S, Alves D R, Quintão N L M, Delle Monache F et al. (2012) Phytochemical analysis and antinociceptive properties of *Garcinia achachairu* Rusby (Clusiaceae) seeds. Arch Pharm Res 35: 623-631.

Examples of Achachairu serum fractions that may be suitable for use in the compositions and methods herein include Recentia® GH (whole fruit) and Recentia® GH-P (peel only) from Ashland Specialty Ingredients. Achachairu peel serum fraction has the INCI designation "*Garcinia Humilis* Peel Extract" and the CAS No. 1622986-60-0. Other examples of Achachairu fractions of the present invention include, without limitation, *Garcinia Humilis* Fruit Extract and *Garcinia Humilis* Juice.

Figure 2:
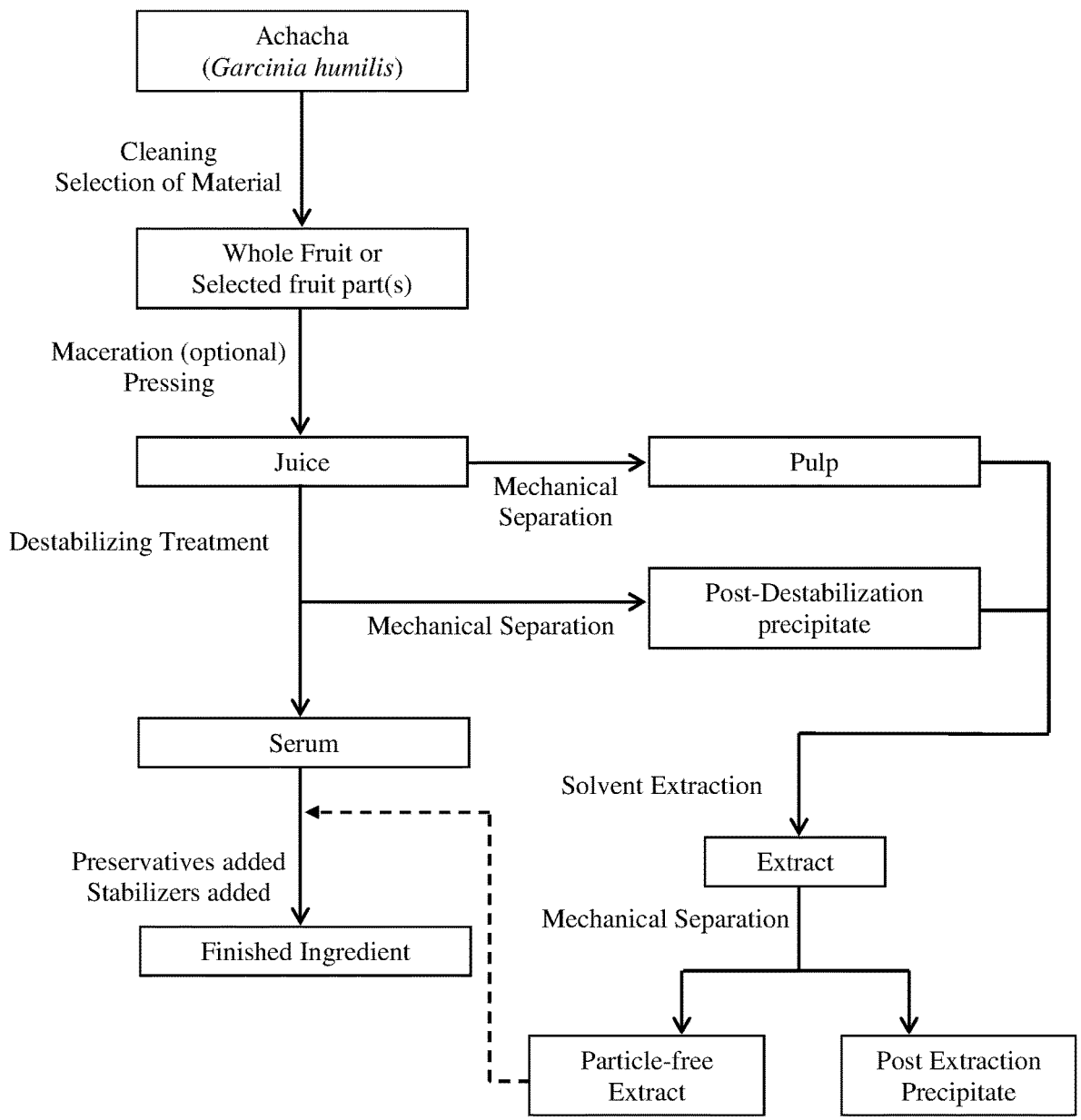
FIG. 2 is a schematic of one embodiment of a process of the present invention for preparing bioactive serum fractions and bioactive fraction extracts derived from an Achachairu (*Garcinia humilis*) plant.
Figure 3A:
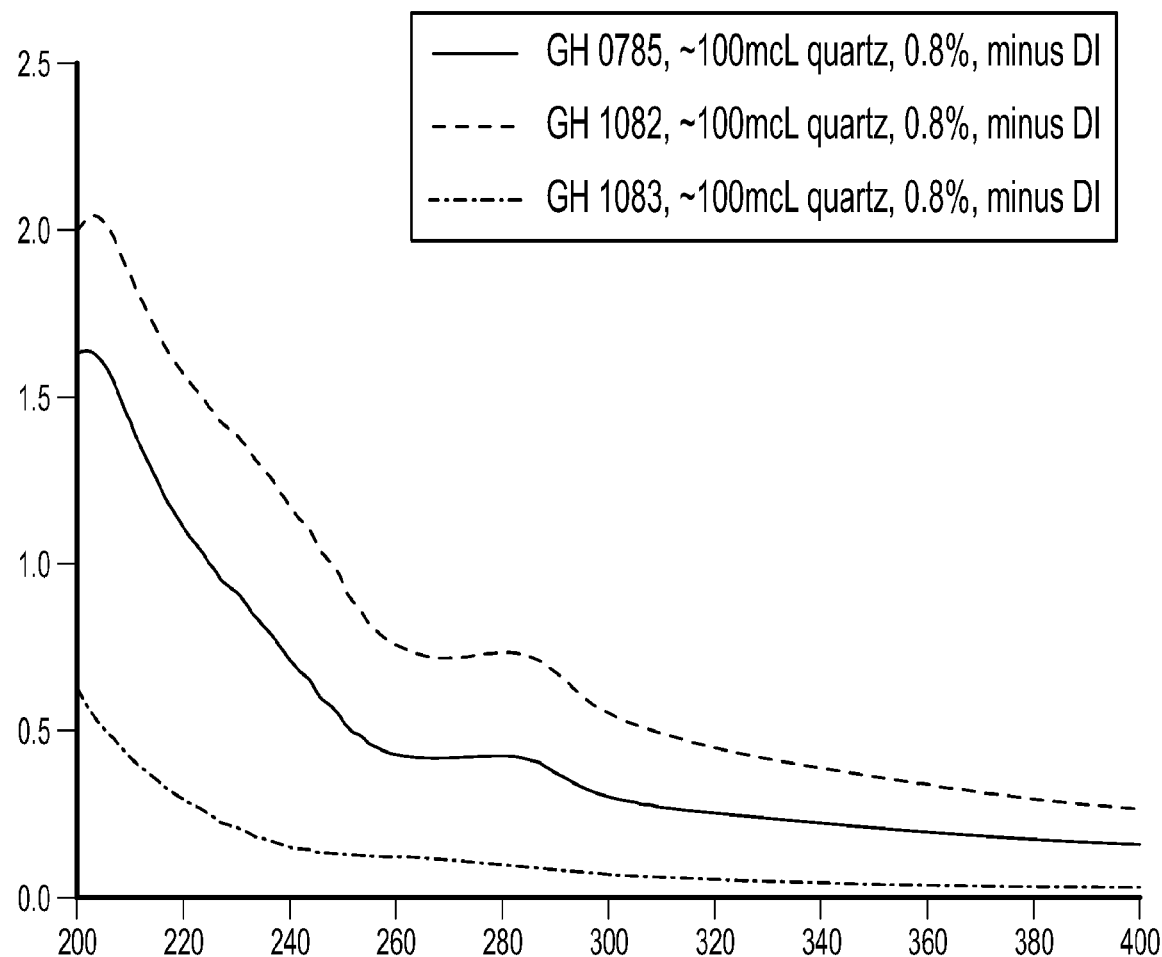
FIGS. 3A-3B are graphs illustrating absorbance spectra data taken from various 100 microliter samples of serum fractions and extracts derived from an Achachairu (*Garcinia humilis*) plant according to one embodiment of the process of the present invention. The serum fractions and extracts analyzed included GH 0785, GH 1082, and GH 1083.
Figure 3B:
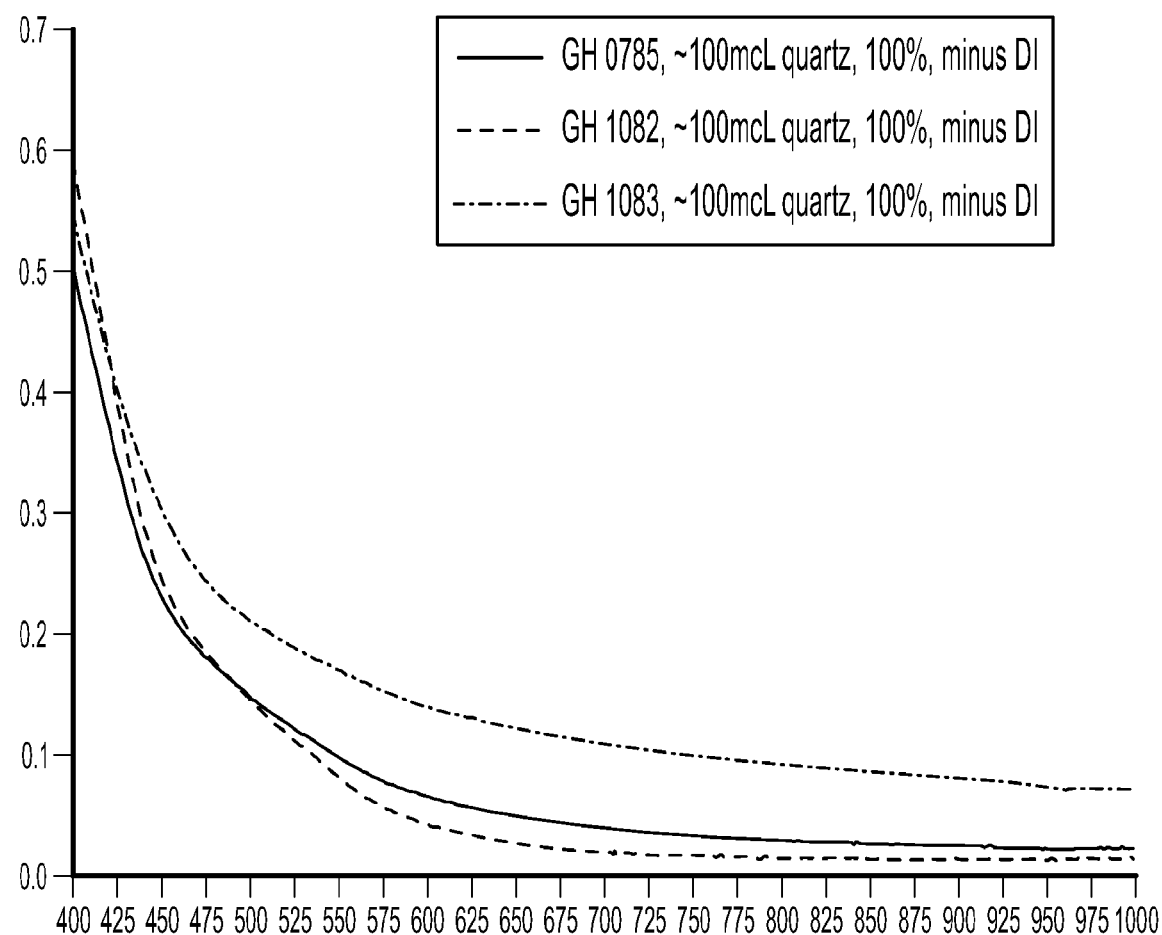
Figure 4A:
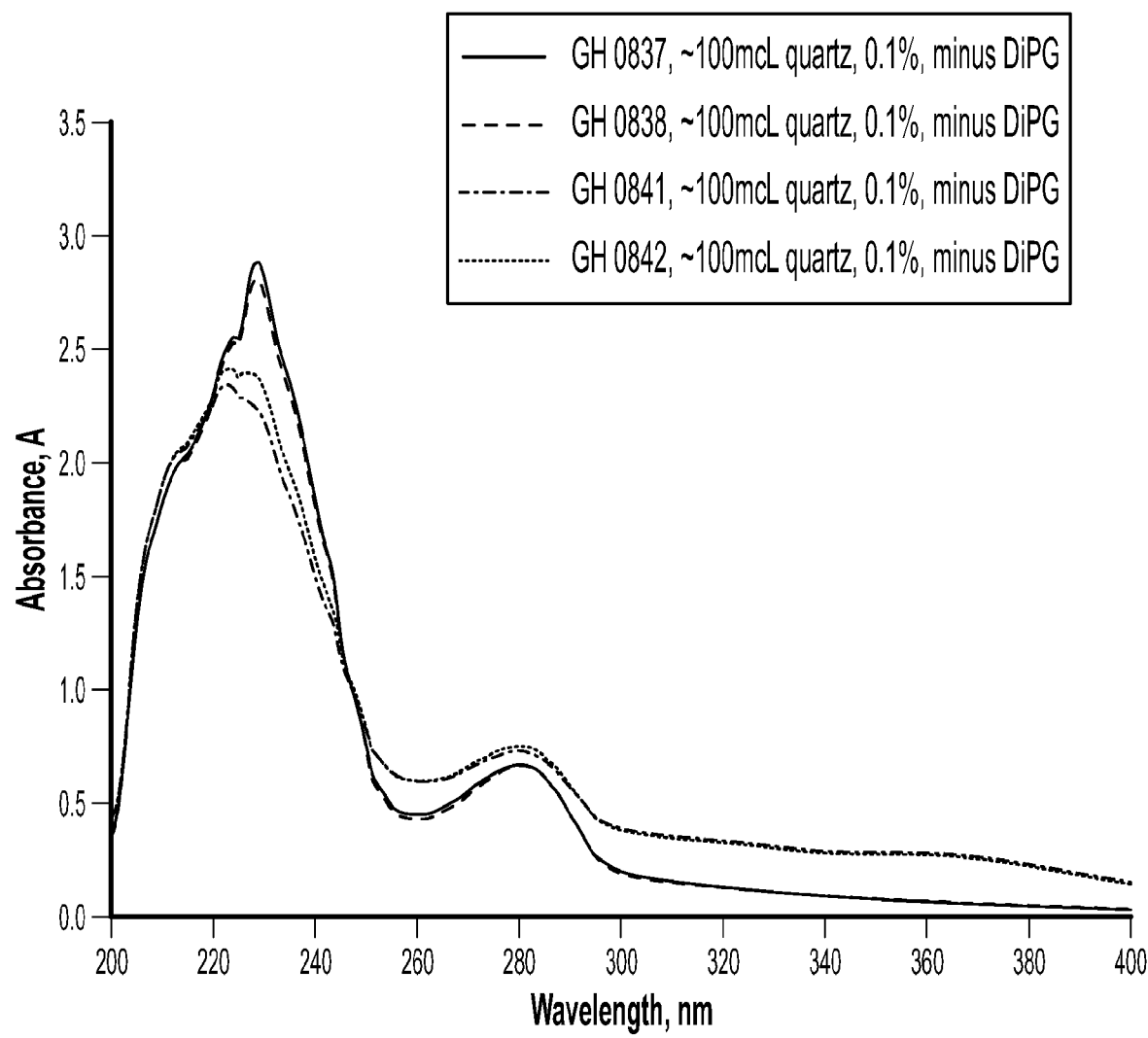
FIGS. 4A-4B are graphs illustrating absorbance spectra data taken from various 100 microliter samples of serum fractions and extracts derived from an Achachairu (*Garcinia humilis*) plant according to one embodiment of the process of the present invention. The serum fractions and extracts analyzed included GH 0837, GH 0838, GH 0841, and GH 0842.
Figure 4B:
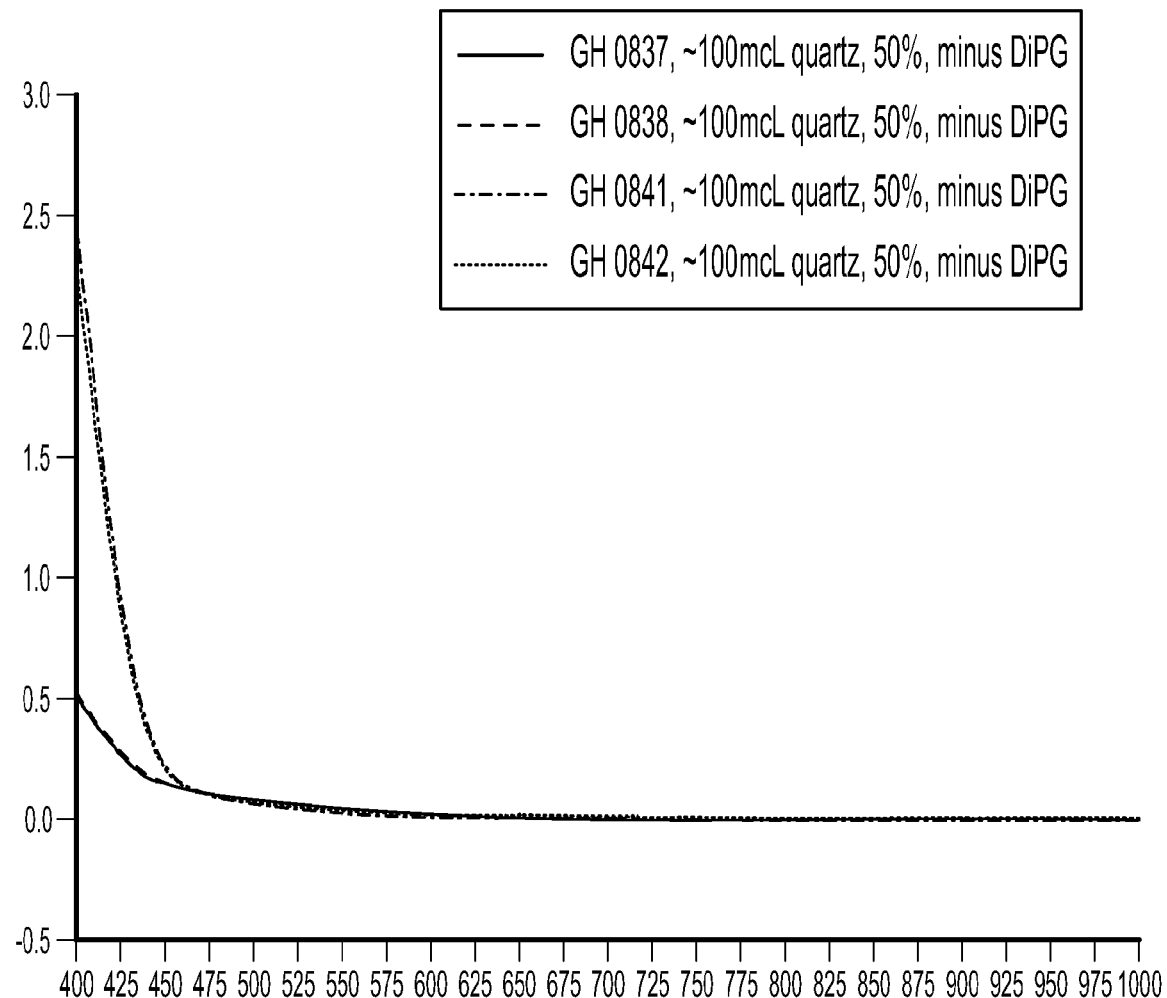
Figure 5:
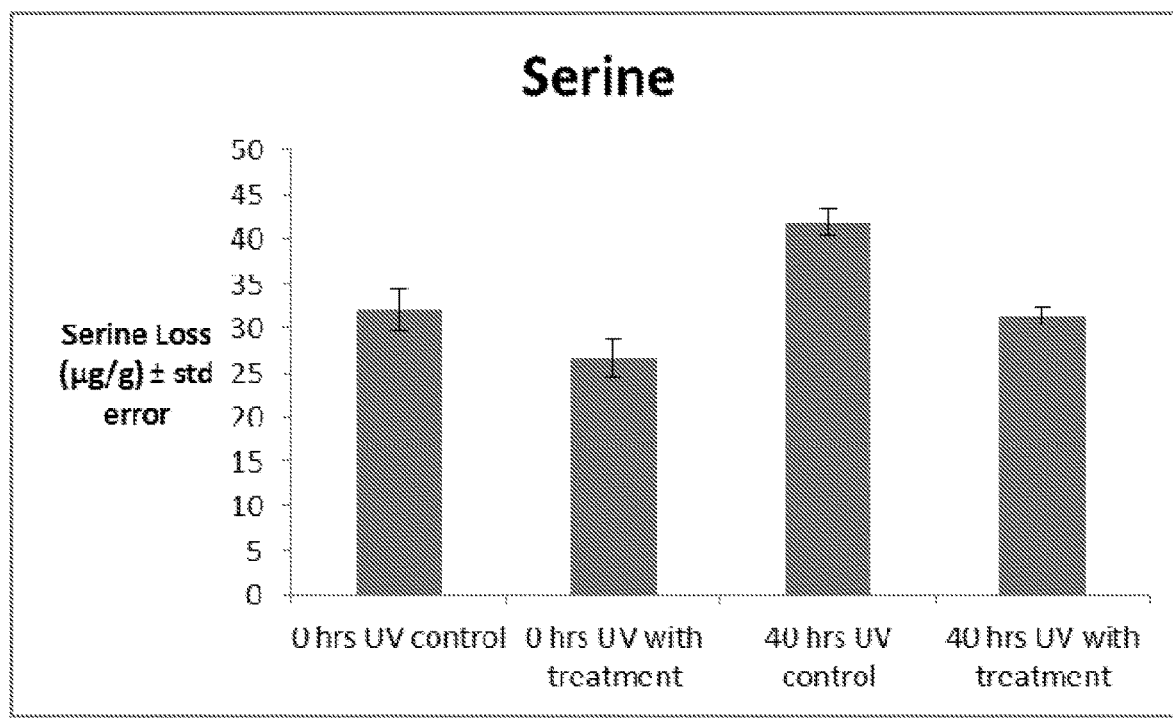
FIGS. 5-8 illustrate the respective amino acid losses for serine, glutamine/glutamic acid, valine, and proline observed in a protein loss assay.
Figure 6:
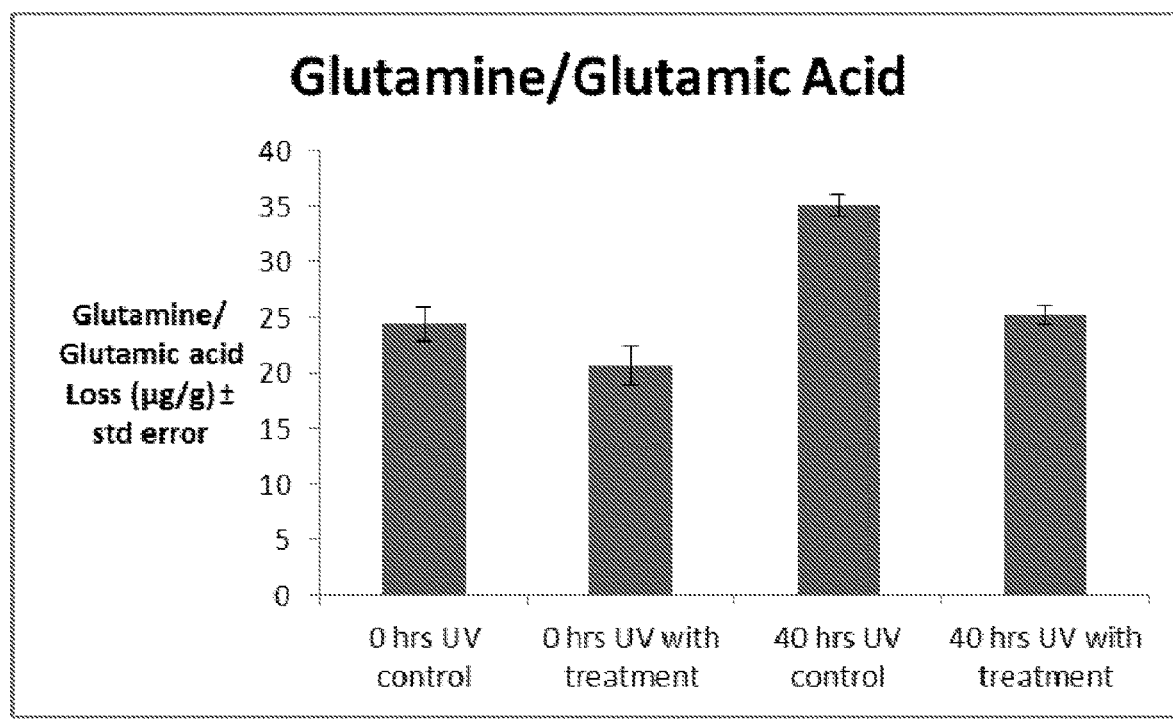
Figure 7:
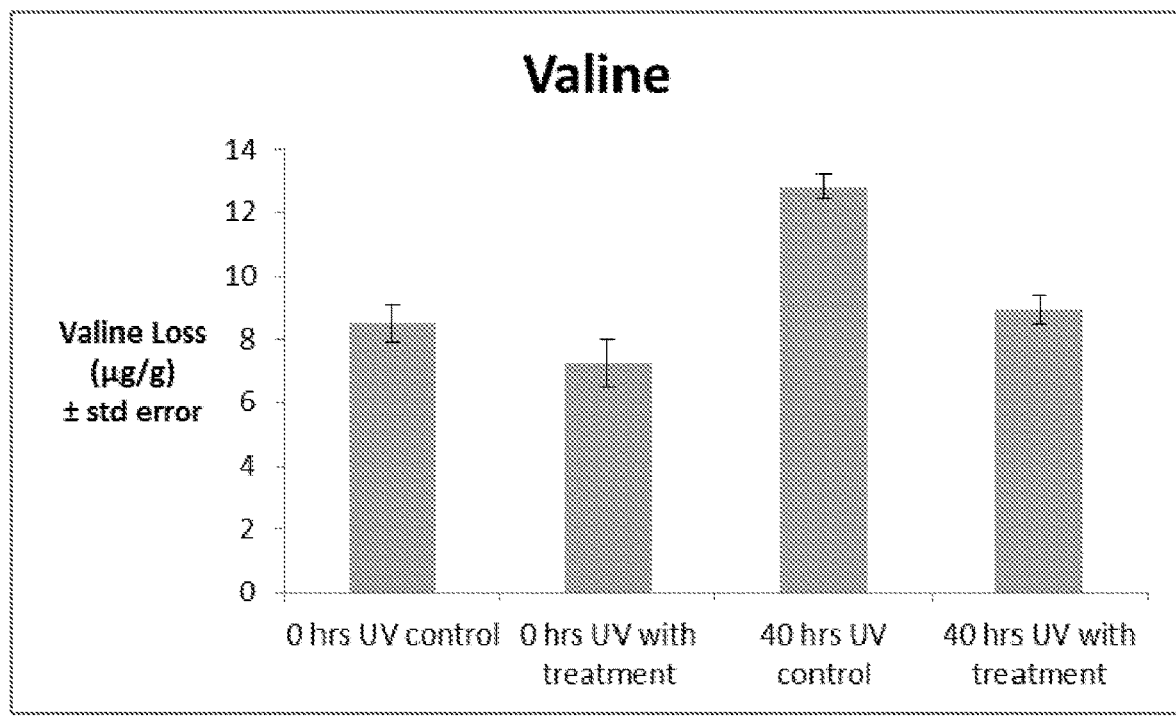
Figure 8:
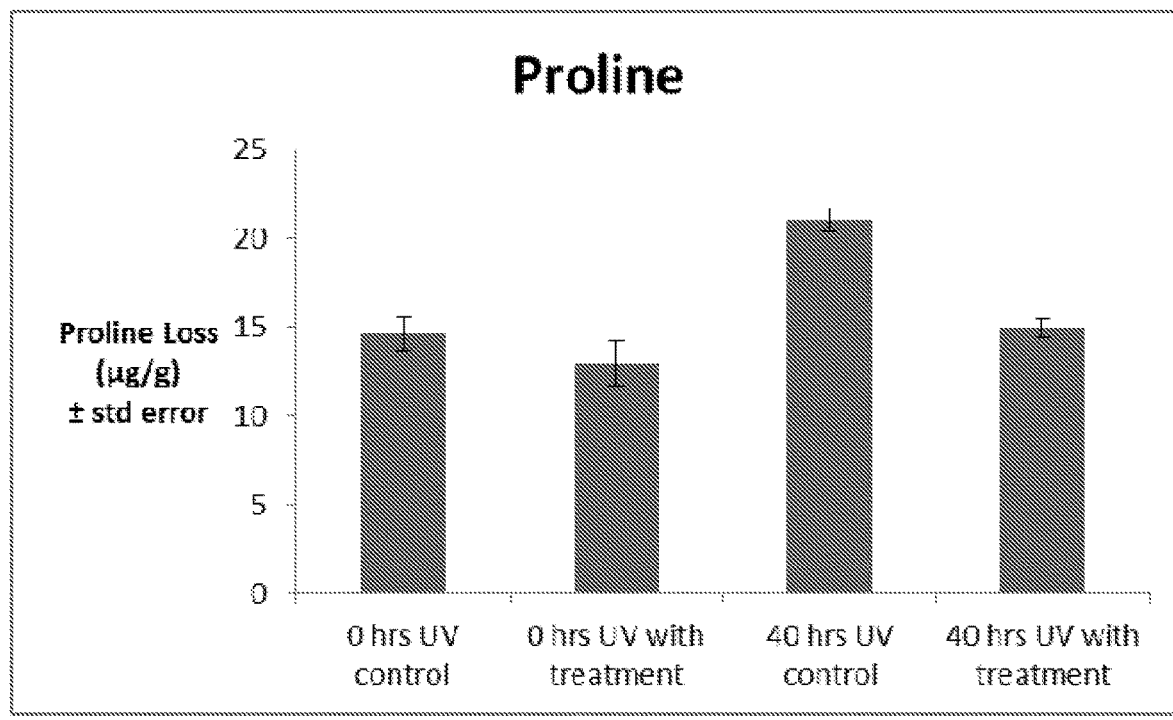
Figure 9:
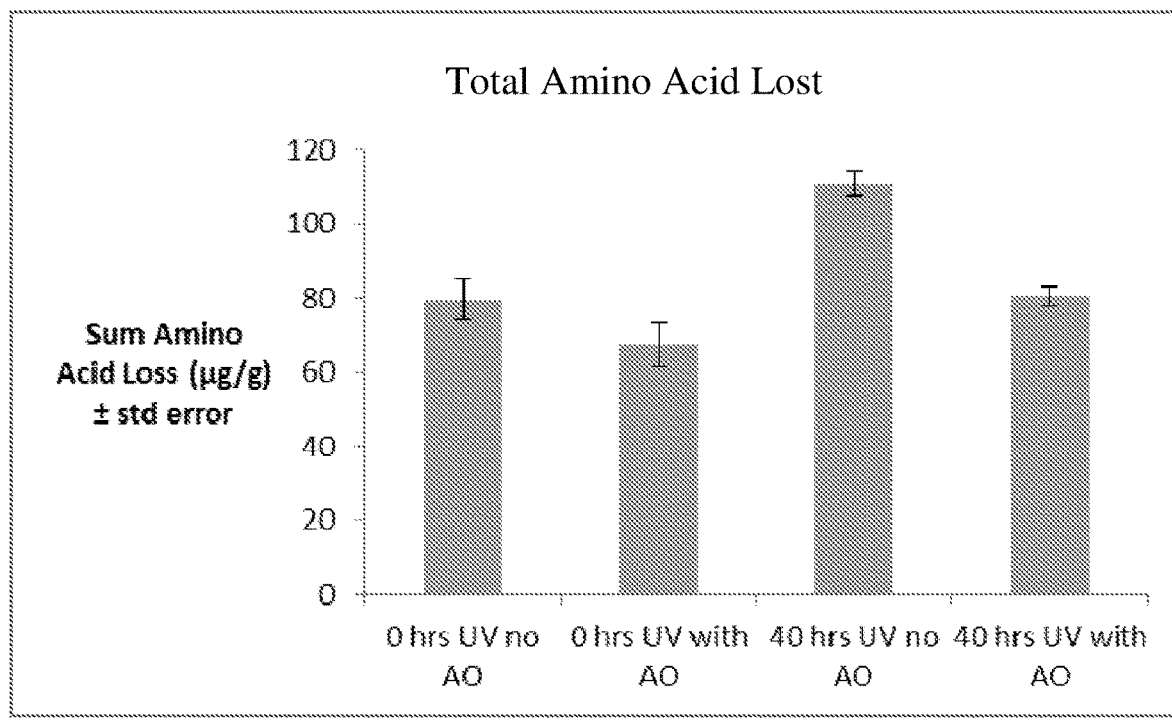
FIG. 9 illustrates the total amino acid loss observed in a protein loss assay.

Methods for Isolating Bioactive Achachairu (*Garcinia humilis*) Serum Fractions and/or Extract In one aspect, the present invention provides a method for isolating bioactive serum fractions and bioactive extracts from the Achachairu (*Garcinia humilis*) plant. FIG. 2 is a schematic of one embodiment of a method for processing of Achachairu (*Garcinia humilis*) fruit to produce bioactive serum fractions, ingredients, and extracts in accordance with the present invention.

As used herein and in the process illustrated in FIG. 2, the term "Cleaning" refers to removal of debris from the harvested fruit and/or leaves prior to further processing, in a way that avoids injury to the fruit, or removal of juice or other valuable components. For example, it can be performed by low-pressure rinsing with potable water, under conditions where residual water wash would not noticeably contain plant pigments. The excess wash water is removed from washed fruit.

As used herein and in the process illustrated in FIG. 2, the term "Selection of material" refers to possible separation of parts of the fruit to further process a particular part alone, or in combination with others. This includes, but is not limited to: whole fruit, peel, flesh and seed. Leaves retained during harvesting of fruit may also be part of selected material.

As used herein and in the process illustrated in FIG. 2, the term "Maceration" refers to an optional step of rendering the fruit and/or selected parts of fruit into smaller particles and otherwise disrupting the integrity of the fruit to ease the following expelling of liquid juice. If the selected material is especially yielding (such as flesh) or otherwise deemed suitable for conditions and equipment of the pressing step, the maceration may be omitted. Examples of suitable maceration implements include, but are not limited to, devices such as a crusher, a grinder, or a mill (e.g., knife mill, hammer mill, etc.). To prevent temperature-induced degradation of fruit material, maceration step can include temperature monitoring and selection of maceration parameters ensuring that there is no significant rise in temperature of fruit material during this step.

As used herein and in the process illustrated in FIG. 2, the term "Pressing" refers to separating liquid material from (optionally macerated) Achachairu fruit or selected parts of Achachairu fruit by application of mechanical force. This includes, but is not limited to, techniques such as draining by ambient gravity, centrifugal force from a rotary expeller, pressure from piston of a hydraulic press, or rollers or a screw of appropriate type of press.

As used herein and in the process illustrated in FIG. 2, the term "Mechanical separation" refers to separating solid and/or semisolid particles and non-aqueous liquid droplets from aqueous liquid by exploiting density and/or size of particles. This includes but is not limited to techniques such as straining, filtration (including filtration utilizing a pressure gradient), skimming, sedimentation by ambient gravity, decanting, centrifugation, or some combination of the above. Continuous flow mechanical separation has been used, but this does not exclude batch processing.

As used herein and in the process illustrated in FIG. 2, the term "Juice" refers to liquid material expelled by pressing Achachairu fruit, or selected parts of Achachairu fruit, and/or leaves with or without removal of pulp. Resulting juice contains a dispersed phase of solid and semi-solid particles and possible droplets of water-immiscible liquids of a variety of sizes (collectively referred to as particles), in a contiguous phase of aqueous serum. These particles, based on size and ease of removal, can be qualitatively described as either "pulp" or "cloud". While details depend on properties of the involved materials (e.g. whole fruit versus selected parts) and exact processing parameters, an example of a size boundary between "pulp" and "cloud" could lie between about 1 and about 100 micrometers.

As used herein and in the process illustrated in FIG. 2, the term "Pulp" refers to both relatively large particles in the juice, and/or same particles removed from the juice by mechanical separation. It is often possible to see and distinguish individual pulp particles with a naked eye. Pulp particles suspended in the juice are amenable to removal by mechanical separation, including, but not limited to, sedimentation by ambient gravity, skimming, passing through a mesh or a filter, or centrifugation.

As used herein and in the process illustrated in FIG. 2, the term "Cloud" refers to relatively small particles in the juice, as well as dissolved compounds (e.g., high molecular weight compounds such as proteins, polysaccharides) which can be readily induced (e.g., by coagulation or temperature change) to form particles. They are typically visible as turbidity of the juice, but it is usually not possible to see and distinguish individual particles without aid of instrumentation. They are dispersed in the juice, with the dispersion remaining stable over a much longer time than pulp suspension. In particular, colloidal components of the cloud may remain stably dispersed for an exceedingly long time. Removal of cloud by trivial means, such as those used for pulp, is notably difficult.

As used herein and in the process illustrated in FIG. 2, the term "Destabilizing treatment" refers to treating material using electromagnetic waves for modifying material's physical properties (such as $\varepsilon_0$ which is the real component of low-frequency dielectric constant). This modification degrades stability of the juice dispersion by causing agglomeration and/or aggregation of particles (especially cloud) into assemblies which are sufficiently large and stable to enable and/or improve their following removal by the following mechanical separation as described above. Continuous flow destabilizing treatment has been used, but this does not exclude batch processing. Treatment duration was selected to be sufficient for effective removal of post-destabilization precipitate via mechanical separation.

As used herein and in the process illustrated in FIG. 2, the term "Serum" refers to contiguous phase of the juice which has been made substantially free of pulp and cloud, as well as possible contaminants of concern.

As used herein and in the process illustrated in FIG. 2, the term "Finished ingredient" refers to serum with added appropriate preservatives and/or stabilizers to protect composition of the ingredient against expected environmental challenges such as temperature, atmosphere (e.g., oxygen), light, and microorganisms. This does not exclude possibility of an ingredient free of preservatives and stabilizers being created by using particular processing and packaging techniques. Separate finished ingredients could also be created based on extracts of Achachairu (*Garcinia humilis*) rather than serum. Particular suitable stabilizing agents can include, without limitation, a preservative, a stabilizer and/or mixtures thereof. The isolated finished ingredient can be further concentrated and then stabilized for further utilization in skin care for topical, oral and functional drink and food applications. The finished ingredients of the present invention can further be included in delivery systems that are commonly used in the art.

As used herein and in the process illustrated in FIG. 2, the term "Post-destabilization precipitate" refers to cloud and any residual pulp which were removed from the juice via mechanical separation following destabilizing treatment.

As used herein and in the process illustrated in FIG. 2, the term "Solvent extraction" refers to combining particles removed from juice with one or more solvents (e.g., fragrance grade dipropylene glycol) under particular conditions (e.g., temperature, agitation, time of exposure, etc.), in order to extract soluble materials. Solvent extraction can be done with pulp particles, with post-destabilization precipitate particles, including cloud, or with their combination.

As used herein and in the process illustrated in FIG. 2, the term "Extract" refers to a solution, in selected solvent or solvents, of particular solutes originating in pulp particles, post-destabilization precipitate particles, or both. The Extract has been mechanically separated from the post-extraction precipitate. In certain embodiments, the Extract may serve as a finished ingredient, or as a base for a finished ingredient via addition of preservatives and stabilizers.

As used herein and in the process illustrated in FIG. 2, the term "Post-extraction precipitate" refers to mechanically separated particles of pulp, post-destabilization precipitate, or both, from which particular solute or solutes have been already extracted using solvent extraction.

The bioactive ingredients of the present invention are either cosmetically acceptable and/or acceptable in functional food and beverage products.

The formulations containing the bioactive fractions (ingredients) of the present invention may be prepared using methodologies that are well known by one of ordinary skill in the relevant art.

Depending on conditions of Achachairu (*Garcinia humilis*) cultivation, year of growth, and particular harvest, the dry matter content in fruit and leaves can vary and it may impact the consistency and reproducibility of derived bioactive fractions (ingredients).

The present invention allows for the standardization of initial plant material properties to improve reproducibility of bioactive (fractions) ingredients by exploring uniform conditions for Achachairu (*Garcinia humilis*) cultivation and harvesting.

An exemplary method of preparing the isolated bioactive fractions derived from Achachairu (*Garcinia humilis*) whole fruit, a particular part of fruit, leaves, or any combination of parts of fruit and/or leaves generally involves three steps, including: (1) a harvesting step; (2) a collecting step; and (3) a washing step.

Prior to undergoing processing, the fresh fruit can be subjected to the following steps: (1) preservation of the inherent moisture content of the fruit; (2) preservation of fruit integrity during harvesting; (3) minimization of environmental impact and time factors of biological degradation of the fruit biomass; and (4) cleaning of the fruit biomass prior to processing (e.g., prior to maceration/grinding).

Suitable techniques to follow for preparing the fresh fruit for the processing are described in more detail, as follows: The harvesting is done with precautions to avoid wilting due to moisture loss. Optimal conditions are those where natural moisture content is maintained and preserved. The harvesting of the plant material is conducted in a manner that avoids or minimizes the chopping, mashing, crushing, or other type of injury of the plant source; for large-scale industrial harvesting, where it may not be possible to avoid chopping due to the type of equipment required, care is taken to minimize injury that could lead to microbial growth, moisture loss, intensification of oxidation, polymerization, isomerization, and hydrolysis processes (i.e., unwanted catabolic processes) in collected plant material.

Further, particular attention is made to minimize injury during and after harvest. Delivery time of the fruit and/or leaves to the processing facility and their exposure to sun, high or low temperature, and other negative environmental factors should be minimized to prevent the impact of unwanted degradation processes as described above. For example, in one embodiment of the present invention, the delivery time for the biomass for further processing does not exceed 30 minutes from the time of harvest. In another embodiment, fruits that undergo long distance transport are treated to a post-harvest procedure involving immediately placing the fruit biomass into styrofoam coolers containing frozen gel packs to help maintain freshness and natural moisture content during overnight delivery to the processing facility. As a non-limiting example, for many fruit species it is beneficial to not only minimize delivery time for processing, but to also keep the fruit and leaves cool, by refrigeration if necessary, to prevent and/or minimize unwanted degradation prior to and/or during processing. In case of tropical fruit it may also be beneficial to avoid excessive cooling.

A cleaning step to remove debris from the fruit and/or leaves prior to further processing is performed once the fruit and/or leaves are harvested. The washing could be achieved using a low-pressure rinse for a short duration under conditions to prevent the initiation of the release of the juice from the fruit, to cause injury, or to remove valuable components. For example, in one embodiment of the present invention, the washing of the fruit was accomplished in less than or equal to 5 minutes with a water pressure of less than or equal to 1 kg/cm$^2$. Residual water wash did not contain plant pigments, which indicated the absence of subsequent injury. The excess water was removed from washed fruit biomass before processing.

After the fruit and/or leaves are harvested, as described above, the further processing of a whole fruit, a particular part of fruit, or any combination of parts of fruit and/or leaves are performed to yield juice. In one embodiment, the whole fruit is subjected to maceration (e.g., grinding), and pressing to separate the intracellular content, i.e., the juice from the pulp. In another embodiment, the fruit peel is subjected to maceration (e.g., grinding) and pressing to separate the juice from the pulp. In another embodiment, the fruit flesh and seed are subjected to maceration (e.g., grinding) and pressing to separate the juice from the pulp. An example of a suitable processing protocol involves the steps described below. A hammer mill may be used to grind the fruit or fruit peel or fruit flesh with seed and or leaves to yield plant material particles of a small size in a short time and without significant increase of biomass temperature. In one embodiment, a modified hammer mill is used to produce the maximum size of macerated whole fruit, a particular part of fruit, or any combination of parts of fruit and/or leaves particles less than or equal to 0.5 centimeters during less than or equal to 10 seconds of treatment, where the increase of biomass temperature is less than or equal to 5° C.

The separation of juice from pulp is commenced promptly, as soon as possible after maceration (e.g., grinding) of the whole fruit, a particular part of fruit, or any combination of parts of fruit and/or leaves and without significant increase in temperature. In one embodiment, immediately after maceration (e.g., grinding), the whole fruit, a particular part of fruit, or any combination of parts of fruit and/or leaves is pressed using a horizontal, continuous screw press. The pressure on the cone is maintained at level 24 kg/cm$^2$, screw speed is at 12 rpm, and biomass temperature increase is less than or equal to 5° C.

Once juice is separated, it contains a dispersed phase of solid and semi-solid particles and possible droplets of water-immiscible liquids of a variety of sizes (collectively referred to as particles), in a contiguous phase of aqueous serum. These particles, based on size and ease of removal, can be qualitatively described as either "pulp" or "cloud". While details depend on properties of the involved materials (e.g., whole fruit versus selected parts) and exact processing parameters, an example of a size boundary between "pulp" and "cloud" could lie between about 1 and about 100 micrometers.

Juice can be used immediately for the further processing. Alternatively, juice is immediately frozen and kept frozen at about minus 30° Celsius. Then, when it is necessary, frozen juice is thawed and processed further.

In one embodiment, mechanically separated juice was subjected to destabilizing treatment by electromagnetic waves in a continuous flow system. The frequency of electromagnetic waves was selected from the range between about 300 MHz and 50 GHz. Suitable devices for generating such electromagnetic waves include, but are not limited to magnetrons, power grid tubes, klystrons, klystrodes, crossed-field amplifiers, travelling wave tubes, and gyrotrons.

Device used in this invention includes magnetrons operating at a frequency of 915 MHz, 2.45 GHz, and 5.8 GHz. The parameters of said electromagnetic waves in destabilization step of the invention allow the value of real component of low-frequency dielectric constant ($\varepsilon'_0$) to be decreased during the treatment by between about 10 and 40 compared to its value prior to treatment.

The value of real component of low-frequency dielectric constant ($\varepsilon'_0$) was determined using broadband dielectric spectroscopy data obtained via equipment and software from Agilent Technologies: PNA-L Network Analyzer N5230C with 85070E dielectric probe kit, N4693-60001 electronic calibration module, and 85070 software. The calculation was performed according to method described in the article Cole, K. S., & Cole, R. H. (1941). Dispersion and absorption in dielectrics I. Alternating current characteristics. The Journal of Chemical Physics, 9(4), 341-351.

After juice destabilization is achieved, its mechanical separation is performed to separate solid and/or semisolid particles and non-aqueous liquid droplets from aqueous liquid by exploiting density and/or on size of particles. This includes but is not limited to techniques such as straining, filtration (including utilizing pressure gradient), skimming, and sedimentation under ambient gravity, decanting, and centrifugation or combinations thereof. Continuous flow mechanical separation has been used, but this does not exclude batch processing.

Serum from the juice of whole fruit, a particular part of fruit, or any combination of parts of fruit and/or leaves is then mixed with at least one preservative, at least one antioxidant and at least one stabilizer to yield a finished ingredient, or combination of thereof. Suitable preservatives, antioxidants and stabilizers for use in the present invention include, but are not limited to tetrasodium EDTA, disodium EDTA, potassium sorbate, sodium benzoate, sodium metabisulfite, sodium methylparaben, glycerin, propylene glycol, di-propylene glycol, butylene glycol, pentylene glycol, hexylene glycol, and caprylyl glycol.

It was unexpectedly found that the process described herein produced finished ingredients with multifunctional biological activities that are either free of or substantially free of benzophenones and proteins.

Solvent Extracts of Achachairu (*Garcinia humilis*)

The present invention also relates to extracts of Achachairu (*Garcinia humilis*) that are prepared, in whole or in part, using conventional solvent extraction techniques.

An Achachairu extract is obtained by separating compounds from Achachairu plant matter with an exogenous solvent. Consistent with the general principle of "like dissolves like," the choice of extraction solvent largely determines the type and number of compounds that will result from any particular extraction technique. For instance, polar compounds are typically extracted out by using polar solvents, while non-polar compounds are extracted out by using non-polar solvents. The correlation between solvent polarity and the types of materials isolated using traditional solvent extraction is described in Houghton & Raman, *Laboratory Handbook for the Fractionation of Natural Extracts* (1998)).

The Achachairu extracts herein may be obtained using any suitable extraction technique known in the art. For example, the Achachairu extract may be obtained by the following procedure: (i) place the desired portion of dried plant material (e.g., whole fruit, fruit pulp, peel, seeds, stem, bark, leaves) in a conical glass percolator; (ii) add the indicated percentage of extraction solvent in a w/w ratio of 1 part plant material to 2 parts extraction solvent (when the indicated percentage of extraction solvent is less than 100%, the remaining solvent is water (e.g., 95% ethanol with 5% water, 50% ethanol with 50% water, etc.); (iii) allow the extraction to proceed for about 16 to about 24 hours; (iv) collect the percolate, and repeat the above process until the resulting percolate is substantially free from plant additional extract; (v) combine the percolates, evaporate to dryness under reduced pressure, and store the resulting extract under nitrogen at less than 4 degrees Celsius. Extracts may be used without any further modification or may be modified (e.g., ethoxylated, esterified) to form a derivative material.

Bioactive Formulations of Achachairu (*Garcinia humilis*) Serum Fractions or Extracts The present invention also relates to a bioactive formulation suitable for topical application to mammalian skin and/or hair. The formulation can be a leave-on product such as, for example, a cream, dressing, gel, lotion, ointment, liquid, a spray applicator, and combinations thereof, or a wash-off product such as for example a hand dishwashing detergent, liquid hand soap, bar soap, body wash, shampoo, general purpose cleanser, and combinations thereof.

In one embodiment, the bioactive topical formulation includes a topically effective amount of the bioactive composition of the present invention. The bioactive topical formulation can further include a topically acceptable carrier. Suitable topically acceptable carriers can include, without limitation, a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and/or a hydrophobic solution base. In one embodiment, the bioactive composition can be present in an amount ranging from between about 0.001 percent and about 99 percent of the total weight of the bioactive topical formulation.

Additional Uses for Achachairu (*Garcinia humilis*) Serum Fractions or Extracts

In another embodiment, the Achachairu serum fractions and extracts can be used in functional beverages, functional food products, supplements, and formulations that include an effective amount of the bioactive composition of the present invention suitable for internal (oral) use. In another embodiment, the bioactive composition can be present in an amount ranging from between about 0.001 percent and about 99 percent of the total weight of the functional beverage, functional food product, and/or supplement.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein. Thus, the following examples are intended to illustrate particular embodiments of the present invention, but are by no means intended to limit the scope of the present invention.

Example 1

Preparation of Bioactive Composition (Finished Ingredient) From Achachairu (*Garcinia humilis*) Whole Fruit The Achachairu (*Garcinia humilis*) whole fruit are collected directly from the trees. Inspection and removal of unsound fruits is conducted. After that the Achachairu fruits are thoroughly cleaned before processing. The whole fruit are then macerated (e.g., grinded), pressed and mechanically separated to produce juice and pulp. The yield of juice from Achachairu (*Garcinia humilis*) whole fruit after maceration (e.g., grinding), pressing and mechanical separation is about 60 to 69% weight/weight; the pH of juice from Achachairu (*Garcinia humilis*) whole fruit is 3.0 to 3.3. The juice was immediately subjected to destabilizing treatment by electromagnetic waves in a continuous flow system that includes magnetrons operating at a frequency of 5.8 GHz. The parameters of said electromagnetic waves in destabilization step of the invention were set to achieve the decrease in the value of real component of low-frequency dielectric constant ($\varepsilon'_0$) during the treatment by about 20 Farads per meter (F/m)—compared to its value prior to treatment. The destabilized juice is immediately pumped through a continuous flow centrifuge to yield a serum and post-destabilization precipitate. It was unexpectedly found that the biological constituents remaining in serum and subsequently in the finished ingredient are substantially free from benzophenones and protein.

Example 2

Preparation of Bioactive Composition (Finished Ingredient) From Achachairu (*Garcinia humilis*) Fruit Peel The Achachairu (*Garcinia humilis*) whole fruit are collected directly from the trees. Inspection and removal of unsound fruits is conducted. After that the Achachairu fruits are thoroughly cleaned before processing. The fruit peel is separated from whole fruits and then macerated (e.g., grinded), pressed and mechanically separated to produce juice and pulp. The yield of juice from Achachairu (*Garcinia humilis*) fruit peel after grinding (maceration), pressing and mechanical separation is about 25 to 35% weight/weight; the pH of juice from Achachairu (*Garcinia humilis*) fruit peel is 2.7 to 3.0. The juice from fruit peel was immediately subjected to destabilizing treatment by electromagnetic waves in a continuous flow system that includes magnetrons operating at a frequency of 2.45 GHz. The parameters of said electromagnetic waves in destabilization step of the invention were set to achieve the decrease in the value of real component of low-frequency dielectric constant ($\varepsilon'_0$) during the treatment by about 30 Farads per meter (F/m)—compared to its value prior to treatment. The de-stabilized juice is immediately pumped through a continuous flow centrifuge to yield a serum and post-destabilization precipitate. It was unexpectedly found that the biological constituents remaining in serum and subsequently in the finished ingredient are free or substantially free from benzophenones and protein.

Example 3

Preparation of Bioactive Compositions (Finished Ingredients) From Achachairu (*Garcinia humilis*) Fruit Flesh and Seeds The Achachairu (*Garcinia humilis*) whole fruit are collected directly from the trees. Inspection and removal of unsound fruits is conducted. After that the Achachairu fruits are thoroughly cleaned before processing. The fruit flesh and seed are separated from whole fruits and then macerated (e.g., grinded), pressed and mechanically separated to produce juice and pulp. The yield of juice from Achachairu (*Garcinia humilis*) fruit flesh and seeds after maceration (e.g., grinding), pressing and mechanical separation is about 30 to 40% weight/weight; the pH of juice from Achachairu (*Garcinia humilis*) fruit flesh and seeds is 3.8 to 4.2. The juice from fruit flesh and seeds was immediately subjected to destabilizing treatment by electromagnetic waves in a continuous flow system that includes magnetrons operating at a frequency of 2.45 GHz. The parameters of said electromagnetic waves in destabilization step of the invention were set to achieve the decrease in the value of real component of low-frequency dielectric constant ($\varepsilon'_0$) during the processing by about 25 Farads per meter (F/m)—compared to its value prior to treatment. The de-stabilized juice is immediately pumped through a continuous flow centrifuge to yield a serum and post-destabilization precipitate. It was unexpectedly found that the biological constituents remaining in serum and subsequently in the finished ingredient are substantially free from benzophenones and protein.

Example 4

Preparation of Extracts From Achachairu (*Garcinia humilis*)

Fruit by Solvent Extraction

Solvent extractions were conducted with pulp particles, with post-destabilization precipitate particles, including cloud, or with their combination using one or more solvents under particular extraction conditions: type of solvent(s), ratio of solvent to plant material (pulp, or post-destabilization precipitate, or their combinations), extraction temperatures, agitation, time of exposure, etc., in order to extract materials that are soluble in the particular solvents.

Pulp, or post-destabilization precipitate, or their combinations to solvent ratio is in the range of 1 part weight of plant material+2 parts weight of solvent to about 1 part weight of plant material+1000 parts weight of solvent. Extraction temperature range is 4° C. to about 100° C. Time of the exposure could vary from about 0.25 hrs to about 96 hrs.

Solvent extract is a solution, in solvent or solvent combinations, of particular solutes originating in pulp particles, post-destabilization precipitate particles, or both.

Extract has been mechanically separated from the post-extraction precipitate. Extract may potentially serve as a finished ingredient, or as a base for a finished ingredient via addition of preservatives and stabilizers.

Example 5

Tests Methods for Determining Effects of Bioactive Ingredients and Extracts of Achachairu (*Garcinia humilis*)

Processes of irritation and inflammation in human skin are often undesirable and can cause lasting cumulative damage which includes visible signs of skin aging (e.g. discoloration and wrinkles), decreased mechanical strength, decreased protective functions, and lessened ability to recover from stress and injuries. These processes can be caused by a variety of stresses and insults to the skin. Especially ubiquitous stresses are sunlight and surfactants. Mitigating irritation and inflammation of the skin, particularly those caused by common stresses, is important and desirable.

Adverse effects of light, most commonly sunlight (though artificial sources are included), on human skin are well known. Overly high exposure to sunlight may cause acute adverse reaction involving irritation and inflammation, such as sunburn. Exposures insufficient to cause acute reactions can still trigger inflammation-related processes. Accumulated inflammatory damage from sunlight exposure causes degradation of skin resilience and development of undesirable appearance, in a process known as photoaging.

Surfactants are used in a variety of personal care and cleansing products to allow or improve processes of cleansing, foaming, emulsifying, solubilizing, and dispersing. Repetitive contact with surfactant-containing products has been shown to cause damage of the skin barrier due to surface or interface activities of the surfactants (Walters R M, Mao G, Gunn E T et al. Cleansing formulations that respect skin barrier integrity. Dermatol Res Pract 2012; 495917: 1-9). The weakened barrier subsequently leads to deeper penetration of the surfactants into skin and induced irritation and inflammation (De Jongh C M, Jakasa I, Verberk M M, Kezic S. Variation in barrier impairment and inflammation of human skin as determined by sodium lauryl sulphate penetration. Br J Dermatol 2006; 154 (4): 651-7. Ananthapadmanabhan K P, Yang L, Vincent C et al. A novel technology in mild and moisturizing cleansing liquids. Cosmetic Dermatology® 2009; 22 (6): 307-16), which can be perceived by consumers as dryness, itchiness, swelling, redness, and pain. As surfactants are widely used in hand soaps, facial and body washes, shampoos and conditioners, as well as dish, laundry and housecleaning detergents, human skin contact with surfactants is frequent.

Irritation and inflammation are commonly viewed as a "cascade" proceeding from necessary release of a signaling compound Interleukin (IL) 1-alpha (or IL-la) to induction of other downstream cytokines and chemokines such as interleukins IL-6 and IL-8 or other signaling molecules (Welss T, Basketter D A, Schroder K R. In vitro skin irritation: facts and future. State of the art review of mechanisms and models. Toxicol In Vitro 2004; 18 (3): 231-43). However, previously published data suggest that "cascade" view might not be a comprehensive model (Koganov, M., Zhang, L., Duev, A., Dueva-Koganov, O., Hou, X., Biological Activities of Novel Ingredients from Living Tea Plant (*Camellia*

*sinensis*), Household and Personal Care Today, 9 (2015) 19-24; and Koganov M, Zhang L, Duev A. Imparting mildness with living tea plant ingredient. Personal Care, 2013; 14(5): 31-4).

Even Sodium Dodecyl Sulfate (SDS), a single compound commonly used as benchmark source of surfactant stress in both in vitro and in vivo studies, can trigger different portions of the irritation and inflammation process without significantly affecting release of a primary cytokine such as IL-1a, depending on concentration. The complexity of irritation and inflammation response of skin cells implies that signaling "network" model is a more adequate analogy than a signaling "cascade" model. This indicates that mitigation of such a complex signaling process must affect more than one pathway, such as by using a multifunctional bioactive ingredient.

One of the methodologies for studying and quantifying irritation and inflammation includes culturing cells of the tissue most likely to come in contact with stress sources, such as viable epidermal keratinocytes from human skin. Human epidermal keratinocytes (HEK) have become the focus of attention in irritant-induced skin inflammation by virtue of their epidermal location, importance in maintaining the integrity of the stratum corneum barrier, and the ability to produce a variety of inflammatory mediators (Weiss T, Basketter D A, Schroder K R. In vitro skin irritation: facts and future. State of the art review of mechanisms and models. Toxicol In Vitro 2004; 18 (3): 231-43). Keratinocytes can release numerous signalling substances such as interleukins in response to a range of irritants including surfactants and sunlight. Amounts of these mediators can then be measured via techniques such as Enzyme-Linked Immunosorbent Assay (ELISA). Bioactive substances capable of reducing HEK release of these inflammatory mediators may help control the signs of irritation and inflammation in human skin.

In addition to interleukins, arachidonic acid metabolites are long known to have significant roles in inflammatory processes. Prostaglandin E2 (PGE2) is one of the most abundant metabolites of arachidonic acid, generated through an enzymatic cascade controlled by cyclooxygenase (COX) enzymes. The importance of PGE2 in inflammation signaling is highlighted by the wide clinical use of COX inhibitors (including those initially of plant origin, such as aspirin) to relieve inflammation.

Besides signalling substances, other very important compounds in processes of irritation and inflammation are those that directly cause the damage. Especially notable inflammatory damage substances are free radicals (especially reactive oxygen species) and protein-degrading enzymes (proteases). It is possible to detect presence or measure the activity of such damaging substances by incubating them with a substrate which they can alter or degrade, with this alteration or degradation being measurable directly (e.g., by loss or development of color or fluorescence), or indirectly (e.g., by ELISA). In some cases, presence or activity of damaging substances themselves can be measured directly or indirectly such as by various spectroscopic techniques (e.g., Electron Paramagnetic Resonance techniques, or chromogenic artificial stable free radicals like DPPH).

Therefore, the tests selected for determining effects of ingredients and extracts of Achachairu (*Garcinia humilis*) include inhibition of proteases (damaging compounds) in non-cell-based bioassays, inhibition of chemokines, cytokines and prostaglandins (signalling compounds) in cultured human skin cells, inhibition of a compound capable of both signalling and causing damage in cultured human cells, and measuring release or lack thereof of substances indicating cell damage or sensitization. The cells used were normal human adult epidermal keratinocytes (HEK). Those knowledgeable in above areas and related conditions as well as other specialties may find other methods of practicing the invention. However, those methods are deemed to be within the scope of this invention.

The following examples illustrate, but do not serve to limit the scope of the invention described herein. They are meant only to suggest a method of practicing the invention. The selection of the in vitro bioassays was based on following rationale: to assure test articles safety by demonstrating the lack of cytotoxicity and sensitization potential; and to determine their efficacy and potency in inhibiting signalling and damaging compounds involved in skin irritation, inflammation and aging processes, for example those induced by various stresses. Stress sources may include important and ubiquitous factors such as sunlight and surfactants.

Example 6

Evaluation of Cytotoxicity (Assessment of Safety)

Lactate Dehydrogenase (LDH) is a key cytoplasmic enzyme. Presence of LDH outside the cells at levels above normal background leakage is an indicator of cell damage or cell death. Assay quantifying LDH in cell culture medium is often employed to assess potential cytotoxicity of test articles and stress factors. Observation of cells under microscope to note cell rupture or changes in cell morphology can also contribute to assessment of cytotoxicity.

Normal human adult epidermal keratinocytes (HEK) and all cell culture supplies were obtained from Life Technologies Co. (Carlsbad, Calif., USA). The cells were grown and then maintained in keratinocyte basal medium 154 (M154) with added human keratinocyte growth supplements (HKGS) at 37° C. in an atmosphere of 5% $CO_2$ and used between passages 2 to 4. For the experiments, HEK cells were trypsinized, seeded in 96-well plates, and grown to ~80% confluence. HEK were then exposed, or not, to a stress factor, and incubated for 16 hours with or without test articles at various concentrations. After incubation, HEK cell supernatant medium samples were collected, and levels of LDH were evaluated using Cytoscan™ LDH Assay kit (Catalog #786-210, produced by G-Biosciences, St. Louis, Mo., USA). Untreated, unstressed HEK cells were lysed using kit-supplied lysis buffer as a positive control, with lysate used as assay positive control and a measure of maximum LDH release. Lower induced LDH release, when confirmed by microscopy, indicates lower cytotoxicity.

Example 7

Evaluation of Skin Sensitization Potential (Assessment of Safety)

It is possible for a test article to not be cytotoxic, and yet be unsafe due to provoking an allergic reaction upon skin contact. Typically, initial exposure to an allergen sensitizes the immune system, and following exposures cause an allergic response. Recent progress in understanding the mechanisms of skin sensitization identified interleukin-18 (IL-18) production in normal human epidermal keratinocytes (HEK) as a useful biomarker for skin contact sensitization (Corsini E, Mitjans M, Galbiati V, Lucchi L, Galli C L, Marinovich M, Use of IL-18 production in a human keratinocyte cell line to discriminate contact sensitizers from irritants and low molecular weight respiratory allergens. Toxicol In Vitro. 2009 August; 23(5):789-96; Teunis M, Corsini E, Smits M, Madsen C B, Eltze T, Ezendam J, Galbiati V, Gremmer E, Krul C, Landin A, Landsiedel R, Pieters R, Rasmussen T F, Reinders J, Roggen E, Spiekstra S, Gibbs S, Transfer of a two-tiered keratinocyte assay: IL-18 production by NCTC2544 to determine the skin sensitizing capacity and epidermal equivalent assay to determine sensitizer potency. Toxicol In Vitro. 2013 April; 27(3): 1135-50). IL-18 is considered a suitable in vitro alternative to animal skin sensitization testing methods such as Local Lymph Node Assay. We therefore evaluated IL-18 production in HEK treated with test articles to determine their sensitization potential.

Normal human adult epidermal keratinocytes (HEK) were cultured as described in Example 6 above. After incubation with test articles or controls for 16 hours, the HEK cells were lysed with 100 µl/well of 0.5% Triton X-100 in pH 7.4 Phosphate Buffered Saline (PBS). The cell lysates were collected, and IL-18 was quantified using Human IL-18 ELISA Kit (Catalog #7620, produced by MBL International Co., Woburn, Mass., USA). A known skin sensitizer, paraphenylenediamine (pPD) used as a positive control, significantly induced IL-18 compared to vehicle control in HEK cultures. Fold changes of IL-18 levels between test articles and respective vehicle controls were calculated and compared to pPD (positive control). Lower induction of IL-18 indicates lower sensitization potential.

Example 8

Inhibition of Trypsin Activity (Assessment of Potency and Efficacy Against Damaging Substance)

Collagen fibers provide most of the mechanical strength and support of the skin. A ubiquitous protease, trypsin, is associated with damage and inflammation. It breaks down collagen, potentially leading to decreased mechanical strength of the skin, as well as wrinkles and darkening after stress or injury (Burns T, Breathnach S, Cox N, Griffiths C. Rook's Textbook of Dermatology. Eighth Edition. Wiley-Blackwell, 2010. Vol. 1 Sections 8.21 to 8.27. Vol. 2 Section 29.7).

Trypsin inhibition by test articles was determined via an EnzChek kit utilizing casein substrate with intra-molecularly quenched fluorescent label moieties (Catalog # E6638, produced by Life Technologies). Testing was conducted according to manufacturer instructions. Digestion buffer concentrate was diluted in deionized water. Substrate and bovine trypsin (Sigma catalog number T9201) were dissolved and diluted in the digestion buffer. Test articles were dissolved and diluted in digestion buffer. Calibration curve was constructed with amounts of trypsin ranging from 1000 nanograms to about 1.4 nanograms in reaction volume. Soybean trypsin inhibitor, type I-S(Sigma) was used as a positive control.

Amount of trypsin in wells with test articles and controls was fixed at 1000 nanograms. $IC_{50}$ was calculated as concentration of test article in the reaction volume (e.g. microtiter plate well) necessary to reduce the trypsin activity to 50%. Lower $IC_{50}$ values indicate higher potency and a degree of efficacy.

Example 9

Inhibition of Elastase Activity (Assessment of Potency and Efficacy Against Damaging Substance)

Elastin is a protein essential to elastic fiber network contained in connective tissues which depend on elasticity for their function, such as skin. Excessive elastase activity, commonly related to inflammation, degrades elastin and decreases strength and resilience of the skin (Burns T, Breathnach S, Cox N, Griffiths C. Rook's Textbook of Dermatology. Eighth Edition. Wiley-Blackwell, 2010. Vol. 1 Sections 8.21 to 8.27. Vol. 2 Section 29.7). During inflammatory processes, elastase can be found in areas beyond those where it is produced or secreted. Human neutrophil elastase inhibition by test articles was determined in kinetic colorimetric assay described by Elastin Products Company, Inc. (Elastin Products Company. Assay with N-MeO-Suc-Ala-Ala-Pro-Val-pNA (EPC No. FH237) as substrate. Elastin Products Company, Inc. Research Biochemicals Catalogue. 2004. p.84) and modified for its use with 96-well microtiter plates (Corning 3641) from Corning, Inc. (Corning, N.Y., USA) and Synergy 2 microplate reader from BioTek Instruments, Inc. (Winooski, Vt., USA). The N-Methoxysuccinyl-Ala-Ala-Pro-Val-pNA substrate (EPC, Catalog No: FH237), and elastase (EPC SE563) were from Elastin Products Company (Owensville, Mich., USA). Working solution of elastase was prepared with 0.15 M pH 7.5 Tris-HCl buffer containing 50 mM NaCl. Working solution of substrate was prepared in 0.15 M pH 5.0 acetate buffer containing 100 mM NaCl, with an aliquot of 2% by volume of final buffer of 1-methyl-2-pyrrolidone used for initial dissolution of the substrate. Deionized water was used to dissolve buffer components. Reaction volume in each well was 224 µl; concentration of elastase was 0.87 units/ml, and substrate, 363 µM.

Enzymatic activity in cleaving the substrate was indicated by a development of yellow color measured as increase in absorbance at 410 nm wavelength. The mean of maximum rate of absorbance increase in negative control wells was considered as 100% of enzyme activity. $IC_{50}$ was calculated as concentration of test article in the well which reduced the elastase activity to 50%. Lower $IC_{50}$ values indicate higher potency and a degree of efficacy.

Example 10

Inhibition of Kallikrein 5 (Assessment of Potency and Efficacy in Reducing Levels of Substance Contributing to Inflammatory Signaling and Damage)

Kallikrein 5 (KLK5), also known as stratum corneum tryptic enzyme, is a trypsin-like serine protease. Recent in vitro and in vivo evidence implicates increased levels of KLK5 in augmented inflammatory response such as rsacea (Two A M, Del Rosso J Q, Kallikrein 5-mediated inflammation in rosacea: clinically relevant correlations with acute and chronic manifestations in rosacea and how individual treatments may provide therapeutic benefit. J Clin Aesthet Dermatol. 2014 January; 7(1): 20-5) and in induction of atopic dermatitis-like lesions (Briot A. et al., Kallikrein 5 induces atopic dermatitis-like lesions through PAR2-mediated thymic stromal lymphopoietin expression in Netherton syndrome. J Exp Med. 2009 May 11; 206(5):1135-47). Normal human adult epidermal keratinocytes (HEK) were cultured as described in Example 6. After incubation with test articles or controls for 16 hours, HEK cell culture supernatants were collected. KLK5 was quantified using a human KLK5 immunoassay Quantikine ELISA kit (Catalog # DKK500, produced by R&D Systems, Minneapolis, Minn.). The changes of KLK5 concentrations between test articles and vehicle controls were calculated and compared. $IC_{50}$ (concentration of test article necessary to reduce KLK5 levels to 50% compared to samples from untreated cells) values were calculated by sigmoidal curve fitting with SigmaPlot 10.0 (Systat Software). Lower $IC_{50}$ values indicate higher potency and a degree of efficacy.

Example 11

Inhibition of IL-6 and/or IL-8 Induced by SDS (Assessment of Potency and Efficacy Against Surfactant-Induced Irritation/Inflammation Signaling Substances)

Normal human adult epidermal keratinocytes (HEK) were cultured as described in Example 6. The cells were then incubated with test articles and/or controls for 16 hours.

Presence of Sodium Dodecyl Sulfate (SDS) in cell cultivation medium at specific concentrations was used for induction of chemokines and cytokines. IL-8 was induced by 6 µg/mL SDS, IL-6 by 12.5 µg/mL SDS. After incubation, HEK cell supernatants were collected. Quantikine® ELISA kits (R&D Systems Inc, Minneapolis, Minn.) were used to quantify these interleukins in the supernatants. IL-8 was quantified by Human CXCL/IL-8 Immunoassay kit (Catalog # D8000C), and IL-6 was quantified by Human IL-6 Immunoassay kit (Catalog # D6050). $IC_{50}$ (concentration of test article necessary to reduce interleukin levels to 50%, with samples from untreated cells considered as 0% and samples treated solely with respective inducing quantity of SDS as 100%) values were calculated by sigmoidal curve fitting with SigmaPlot 10.0 (Systat Software). Lower $IC_{50}$ values indicate higher potency and a degree of efficacy.

Example 12

Inhibition of IL-6 and/or IL-8 and/or PGE2 Induced by Full-Spectrum Sunlight from Artificial Source (Assessment of Potency and Efficacy Against Sunlight-Induced Irritation/Inflammation Signaling Substances)

Normal human adult epidermal keratinocytes (HEK) were cultured as described in Example 6. The cells were washed once, and M154 was replaced with PBS. Both the washing and the replacement were done with PBS, to remove light-absorbing components of M154. The 96-well plate containing HEK was then covered with UV-transparent 1 mm quartz sheet, placed on white underlay atop controlled Peltier-cooled surface maintaining room temperature, and irradiated with a dose of 20 $J/cm^2$ of artificially produced full spectrum sunlight at dose rate of about 1100 $W/m^2$, as measured via pyranometer through same quartz cover. PBS was then removed and replaced with M154, and cells were incubated with test articles and/or controls for 16 hours. Identical manipulations, with exception of presence of sunlight, were carried out with HEK serving as unstressed controls. Irradiation equipment was obtained from Solar Light Company, Glenside, Pa. and included Solar Simulator LS1000-6R-002 in Airmass 1.5 configuration using plain mirror; XPS1000 precision current source, and PMA2144 Pyranometer. After incubation, HEK cell supernatants were collected. Quantikine® ELISA kits (R&D Systems Inc, Minneapolis, Minn.) were used to quantify interleukins in the supernatants. IL-8 was quantified by Human CXCL/IL-8 Immunoassay kit (Catalog # D8000C), IL-6 was quantified by Human IL-6 Immunoassay kit (Catalog # D6050); and PGE2 was quantified using Parameter™ Prostaglandin $E_2$ Assay (Catalog # KGE004B). $IC_{50}$ (concentration of test article necessary to reduce interleukin or prostaglandin levels to 50%, with samples from non-irradiated cells considered as 0% and from irradiated cells considered as 100%) values were calculated by sigmoidal curve fitting with SigmaPlot 10.0 (Systat Software). Lower $IC_{50}$ values indicate higher potency and a degree of efficacy.

Example 13

Physico-Chemical Characteristics of Serums and Finished Ingredients: Methods of Evaluation Various methods were conducted to test and evaluate the physico-chemical characteristics of serum fractions and finished ingredients produced according to embodiments of the process of the present invention. The test methods are described in Table 1, below.

TABLE 1

| Physico-Chemical Methods of Evaluation | | |
|---|---|---|
| Property | Test Method | Units |
| Appearance | Determined organoleptically. | N/A |
| Odor | Determined organoleptically. | N/A |
| Color | Determined on Lovibond Comparator 3000 Gardner Scale. Turn on comparator lamp. Measure 8 mL of sample into sample tube. Insert tube into comparator. Rotate the knobs until two color standards nearest in color to the sample have been located. Record the value of the sample color accordingly. If the color of the sample is substantially similar to both, rather than a single standard, then record it as a value between the values of the two standards. | Gardner scale |
| Dry Matter | Dry matter is determined by comparing the weights of liquid sample with residual dry matter after water has been evaporated. Procedure is based on standard laboratory practices commensurate with available equipment. Take three disposable aluminum weighing dishes (VWR 25433-016) and distinctly number them with a permanent marker on the outside. Allow marker ink to dry. Turn on the Ohaus Explorer E00640 balance (Ohaus Corporation) and allow it to start up. Zero the weight. Place a dish on the balance and record the weight for that dish as 'tare'. Without removing the dish from the balance, add approximately 4 mL of liquid sample and | % |

TABLE 1-continued

Physico-Chemical Methods of Evaluation

| Property | Test Method | Units |
|---|---|---|
| | record the weight for that dish as 'tare + wet'. Set the dish with sample aside. Repeat the above with two remaining dishes. Leave the dishes for 24 hours in the ThermoScientific "Lindberg Blue M" Gravity oven at 105 degrees Celsius. Remove the dishes and allow them to cool for approximately 5 minutes at room temperature. Weigh each dish with dried residue individually and record the weight as 'tare + dry'. Dry matter percentage is calculated as ('tare + dry' − 'tare')/('tare + wet' − 'tare') * 100. Record dry matter percentage for the sample as mean of dry matter percentage for the three dishes. | |
| Refractive index | Determined by measuring on Reichert Arias 500 refractometer with temperature regulation provided by Cole-Parmer Polystat temperature controller, model number 12108-10. Procedure is based on the instruction manual for Arias 500 refractometer, sections 6.0, 4.1 and 4.4-4.5. Turn on the temperature controller, set temperature to 20 degrees Celsius. Turn on refractometer. Ensure that Automatic Reading Method is enabled. Deposit approximately 0.5 mL of deionized water on the surface of the lower measuring prism. Close the cell, taking care to avoid bubble formation. Turn shadowline adjustment knob to bring the shadowline within the crosshairs. Wait for temperature at refractometer measuring cell to completely stabilize, then push Read button. Retry above steps until refractive index of deionized water is determined as 1.333 at least three times in a row. Rinse the lower and upper surfaces of the measuring cell with deionized water and blot dry with lint-free wipe. Deposit approximately 0.5 mL of sample on the surface of the lower measuring prism. Close the cell and turn the shadowline adjustment knob to bring the shadowline within the crosshairs. Wait for temperature at refractometer measuring cell to completely stabilize, then push Read button and note the reading. Rinse the lower and upper surfaces of the measuring cell with deionized water and blot dry with lint-free wipe. Repeat above steps until stable readings have been obtained for sample material at least three times in a row. Record the value of these stable readings as refractive index of the sample material. | nD |
| Density | Determined with Densito 30PX densitometer from Mettler Toledo. Procedure is based on Operating Instructions for Densito 30PX, sections 4 and 6. Push and hold the power button on the densitometer for a second to turn it on. Once the instrument starts up, ensure that the display is set to g/cm3 units. Depress the plunger button fully, submerge the sampling tube in deionized water and slowly push the fill trigger to fill the sample loops with 4 cm3 of deionized water. Avoid bubble intake or formation. Note the reading. If it deviates by more than 0.05% from expected density of water at the ambient temperature, recalibrate the densitometer as per Operating Instructions. After ensuring that the unit display and calibration for densitometer are proper, eject the water into a waste receptacle by depressing the plunger button fully. Submerge the sampling tube in liquid sample and push the fill trigger to fill the sample loops with 4 cm3 of sample. Avoid bubble intake or formation. Note the reading once it stabilizes. Eject the sample from densitometer into a waste receptacle and repeat steps above for additional readings, until receiving three matching readings in a row. Record that as the value of density (specific gravity) for the sample. | $g/cm^3$ |
| pH | Determined by measuring on a pH meter such as Denver Instrument Model 250 pH/ISE/conductivity meter with pH/ATC electrode number 300729.1. Procedure is based on Denver Instrument Company 301127.1 Rev. D manual, pages ii and 9 through 12. The pH 4.01 and pH 7.00 buffers used to calibrate the pH meter during the product specification determination were acquired from Thermo Electron Company. | N/A |
| Total Plate Count | Determined as per US Pharmacopoeia XXX, NF25, <61>, Microbiological Limit Tests | CFU/gm |
| Mold/Yeast | Determined as per US Pharmacopoeia XXX, NF25, <61>, Microbiological Limit Tests | CFU/gm |

TABLE 1-continued

Physico-Chemical Methods of Evaluation

| Property | Test Method | Units |
|---|---|---|
| E. coli | Determined as per US Pharmacopoeia XXX, NF25, <61>, Microbiological Limit Tests | CFU/gm |
| Salmonella sp. | Determined as per US Pharmacopoeia XXX, NF25, <61>, Microbiological Limit Tests | CFU/gm |
| Staphylococcus aureus | Determined as per US Pharmacopoeia XXX, NF25, <61>, Microbiological Limit Tests | CFU/gm |
| Pseudomonas sp. | Determined as per US Pharmacopoeia XXX, NF25, <61>, Microbiological Limit Tests | CFU/gm |
| Benzophenones, e.g. Guttiferone A | Dal Molin M M, Silva S, Alves D R, Quintão N L M, Delle Monache F et al. (2012) Phytochemical analysis and antinociceptive properties of Garcinia achachairu Rusby (Clusiaceae) seeds. Arch Pharm Res 35: 623-631. | % |
| Protein | Amino acid analysis conducted on Hitachi L-8900 amino acid analyzer. | % |

Example 14

Physico-Chemical Characteristics of Serums and Finished Ingredients

Results of physico-chemical characteristics of various serum fractions and finished ingredients produced according to embodiments of the process of the present invention as shown in Table 2, Table 3, and Table 4, below.

TABLE 2

Physico-Chemical Characteristics of Serums

| | Serums obtained from: | | |
|---|---|---|---|
| | Whole Fruit Lot GH 0785 | Fruit Peel Lot GH 1082 | Fruit Flesh & Seed Lot GH 1083 |
| Appearance | Clear Orange Liquid | Clear Orange Liquid | Hazy Yellow Liquid |
| Odor | Characteristic | Characteristic | Characteristic |
| Color (Gardner Scale) | 6.5 | 8.5 | 6.5 |
| Dry matter (%) | 13.05 | 11.02 | 16.3 |
| Refractive index (nD) | 1.355 | 1.352 | 1.359 |
| pH | 3.06 | 2.85 | 4.03 |
| Density, g/cm$^3$ | 1.0612 | 1.0514 | 1.0714 |
| Protein | <0.07% | <0.13% | <0.15% |
| Benzophenones | <0.1% | <0.1% | <0.1% |

TABLE 3

Physico-Chemical Characteristics of Extracts

| | Extracts (1 part plant material + 3 part solvent ratio, weight/weight) obtained from: | | | |
|---|---|---|---|---|
| | Whole Fruit Extracted at 4° C. Lot. GH 0841 | Fruit Peel Extracted at 4° C. Lot GH (PE) 0837 | Whole Fruit Extracted at 40° C. Lot. GH 0842 | Fruit Peel Extracted at 40° C. Lot GH (PE) 0838 |
| Appearance | Orange Liquid | Orange Liquid | Orange Liquid | Orange Liquid |
| Odor | Characteristic | Characteristic | Characteristic | Characteristic |
| Color (Gardner Scale) | 11.0 | 12.5 | 11.5 | 13.5 |
| Refractive index (nD) | 1.4315 | 1.4291 | 1.4314 | 1.4291 |
| Protein | <0.046% | <0.049% | <0.041% | <0.046% |
| Benzophenones | About 0.1% | <0.1% | About 0.1% or higher | <0.1% |

Finished Ingredient Recentia® GH-P (CAS RN#1622986-60-0) was prepared according to the process described in Example 2. Physico-chemical and microbial characteristics of Recentia® GH-P are provided in Table 4, below.

TABLE 4

Recentia ® GH-P Physico-Chemical and Microbial Specifications

| Test Parameter | Result |
|---|---|
| Appearance | Clear Orange Liquid |
| Odor | Characteristic |
| Solubility in water | Soluble in any ratio |
| Color (Gardner scale) | 5-12 |
| Dry matter (%) | 9.0-12.1 |
| pH | 2.9-3.8 |
| Refractive index (nD) | 1.349-1.355 |
| Total Plate Count (CFU/g) | <100 |
| Mold/Yeast (CFU/g) | <100 |
| E. coli (CFU/g) | Negative/10 g |
| Salmonella sp. (CFU/g) | Negative/10 g |
| Staphylococcus aureus (CFU/g) | Negative/10 g |
| Pseudomonas sp. (CFU/g) | Negative/10 g |

Example 15

Absorbance Spectra of 100 Microliter Samples of Serum Fractions and Extracts of Achachairu (*Garcinia humilis*)

Absorbance spectra (in wavelength ranges 200-400 nm and 400-1000 nm) were obtained using Synergy 2 multi-mode microplate reader (BioTek Instruments, Inc) with 96-well black quartz microplate (Hellma Analytics GmbH).

All dilutions were done as volume/volume. Spectra of 100 microliter aliquots of respective solvents (ultrapure deionized water and fragrance grade dipropylene glycol) were subtracted from sample spectra. Absorbance spectra results are shown in FIGS. 3A, 3B, 4A, and 4B.

Example 16

Biological Activities of Serums and Finished Ingredients of Achachairu (*Garcinia humilis*)

Various serums and finished ingredients prepared according to an embodiment of the process of the present invention were tested for certain biological activities.

Table 5 includes data of certain serums and finished ingredients using the following tests: IL8/full spectrum sun induction; PGE2/full spectrum sun induction; and cytotoxicity (LDH/microscopy).

TABLE 5

Biological Activity Results Using IL8, PGE2, and Cytotoxicity Assays

| Material | IL8/full spectrum sun induction | PGE2/full spectrum sun induction | Cytotoxicity (LDH/microscopy) |
|---|---|---|---|
| Achachairu (*Garcinia humilis*) Whole Fruit Extract, Lot 0841 | Some inhibition at low concentrations (~25% inhibition at 0.01%); shows induction/cytotoxicity in high concentrations. | Inhibits at low concentrations, $IC_{50}$ ~0.01%; induces/cytotoxic at high concentrations. | At concentrations 0.1% and above it is cytotoxic. |
| Achachairu (*Garcinia humilis*) Fruit Peel Extract, Lot 0837 | Inhibition at low concentrations (estimated $IC_{50}$ 0.012%, max inhibition ~66% at 0.05%). Shows induction/toxicity in high concentrations. | Inhibits at low concentrations, $IC_{50}$ ~0.04%; induces/cytotoxic at high concentrations. | At concentrations 0.23% and above it is cytotoxic. |
| Achachairu (*Garcinia humilis*) Fruit Peel Serum Fraction, 1082 | No significant inhibition. Induces/cytotoxic in high concentrations | $IC_{50}$ between 0.003-0.03%. Maximum inhibition ~70% at 0.001%; induces/cytotoxic at high concentrations. | At concentrations 0.23% and above it is cytotoxic |
| Achachairu (*Garcinia humilis*) Whole Fruit Serum Fraction, Lot 0785 | No significant inhibition. Induces/cytotoxic in high concentrations. | Maximum inhibition ~40% at 0.01%; induces at high concentrations. | At concentrations 0.23% and above it is cytotoxic. |
| Achachairu (*Garcinia humilis*) Fruit Flesh + Fruit Seed Serum Fraction, Lot 1083 | No significant inhibition. Induces in high concentrations. | Non-significant inhibition at 0.01-0.02%; non-significant induction at high concentrations. | At concentrations up to 0.5% it is not cytotoxic. |

Table 6 includes data of certain serums and finished ingredients using the following tests: IL8/SDS induction; KLK5/baseline; IL18/baseline; cytotoxicity (LDH/microscopy); trypsin inhibition; and elastase inhibition.

TABLE 6

Biological Activity Results Using IL8, KLK5, IL18, Cytotoxicity, Trypsin Inhibition, and Elastase Inhibition Assays

| Material | IL8/SDS induction | KLK5/ Baseline | IL18/ Baseline | Cytotoxicity (LDH/ microscopy) | Trypsin Inhibition | Elastase Inhibition |
|---|---|---|---|---|---|---|
| Achachairu (*Garcinia humilis*) Fruit Peel Serum Fraction, Lot 0822 | Not tested | $IC_{50}$ ~0.18% | Maximum 1.46 fold (benchmark sensitizer 7.8 fold) | No cytotoxicity at 0.1% | $IC_{50}$ ~0.37% | $IC_{50}$ ~0.26% |
| Achachairu (*Garcinia* | About 65% inhibition at | $IC_{50}$ ~0.2% | Maximum 1.8 fold | No cytotoxicity | $IC_{50}$ ~0.32% | $IC_{50}$ ~0.28% |

TABLE 6-continued

Biological Activity Results Using IL8, KLK5, IL18, Cytotoxicity, Trypsin Inhibition, and Elastase Inhibition Assays

| Material | IL8/SDS induction | KLK5/ Baseline | IL18/ Baseline | Cytotoxicity (LDH/ microscopy) | Trypsin Inhibition | Elastase Inhibition |
|---|---|---|---|---|---|---|
| humilis) Whole Fruit Serum Fraction, Lot 0786 | 0.1% | | | (benchmark sensitizer 7.8 fold) | at 0.1% | |

In summary, biological activity results showed that preparations of Achachairu (Garcinia humilis): (i) are not potential skin sensitizers according to in vitro test; (ii) are not cytotoxic in vitro at selected concentrations that could be relevant to their concentrations in finished product formulation; and (iii) show in vitro activities indicating potential usefulness for mitigating signs of skin aging caused by inflammation and related process (e.g., those triggered by stresses to the skin, including environmental stress such as full-spectrum sun exposure).

More specifically, test results showed the following: (i) against PGE2, Achachairu (Garcinia humilis) Whole Fruit Extract is slightly more effective than Fruit Peel Extract; (ii) against PGE2, Achachairu (Garcinia humilis) Fruit Peel Serum Fraction is more effective than Whole Fruit Serum Fraction, which is tentatively better than Fruit Flesh+Fruit Seed Serum Fraction; (iii) Achachairu (Garcinia humilis) Whole Fruit Serum Fraction is effective against SDS-induced IL-8, but not against sun-induced IL8, which is surprising. Surprisingly potent inhibition was demonstrated by: (i) Achachairu (Garcinia humilis) Fruit Peel Extract against sun-induced IL8; and (ii) Achachairu (Garcinia humilis) Fruit Peel Serum Fraction against sun-induced PGE2. Furthermore, Achachairu (Garcinia humilis) Fruit Flesh+Fruit Seed Serum Fraction has not demonstrated any notable activities, which is surprising. Achachairu (Garcinia humilis) Fruit Peel Serum Fraction and Whole Fruit Serum Fraction are more cytotoxic than Fruit Flesh+Fruit Seed Serum Fraction. Achachairu (Garcinia humilis) Whole Fruit Extract is more cytotoxic than Fruit Peel Extract.

Example 17

Anti-Oxidant Response Element Activation

This example demonstrates the ability of Achachairu to activate the anti-oxidant response element ("ARE") of a cell. The ARE is the so-called "master switch" believed to control the antioxidant defense system of most cells. When the ARE is activated in response to oxidative stress, the corresponding genes signal the cell to begin producing reduction/oxidation regulators and/or reactive oxygen species ("ROS") quenching proteins and enzymes. ROS are highly reactive molecules formed naturally within cells as a natural byproduct of the normal metabolism of oxygen and play a role in cell signaling and homeostasis. However, when a cell is exposed to a stressor such as heat or UV radiation, ROS levels can increase, and in some instances dramatically. As the damage caused by ROS accumulates over time, it causes more and more oxidative stress at the cellular level that ultimately may lead to tissue damage and/or organ dysfunction. Thus, without being limited by theory, it is believed that if Achachairu can demonstrate the ability to activate the ARE, then personal care compositions containing Achachairu may help fight cellular damage associated with oxidative stress.

In this example, ARE activation was quantitated using the ARE-32 reporter cell line available from CXR-Biosciences as described in the method below. ARE-32 is a stable MCF7 cell line containing pGL8x-ARE (8 copies of the rat GST ARE linked to the luciferase gene) and pCDNA3.1, which contains the neomycin selectable marker. Selection was performed in the presence of G418 and resistant clones were isolated. Clones were screened for induction of luciferase in response to tBHQ.

The ARE-32 cells are maintained routinely in Dulbecco's Modified Eagle Medium (phenol red free) ("DMEM") containing: 10% fetal bovine serum ("FBS"), 50 units/ml penicillin & 50 µg/ml streptomycin, 0.8 mg/ml G418. Cells are subcultured every 3-4 days. If needed, cells can be frozen in medium that contains 90% FBS and 10% DMSO.

Method

In a 96 well-plate, $1 \times 10^4$ cells/well were seeded in 100 µl DMEM containing 50 units/ml penicillin, 50 µg/ml streptomycin, 0.8 mg/ml G418 and 10% FBS. Next, the cells were incubated at 37° C. in a 5% $CO_2$ incubator for 24 hours, and then the medium was replaced with 100 µl fresh media. The test samples were treated with Achachairu serum fractions at the concentration listed in Table 7 (1 microliter per well), the positive control was 25 ump TBHQ. (10 millimolar tBHQ of stock solution freshly prepared in DMSO). 100 microliters of media was added after treatment for a final assay volume of 200 microliters. The cells were incubated at 37° C. in $CO_2$ incubator for another 24 hrs. The test samples were then assayed for luciferase activity with Steady-Glow™ brand assay system according to the manufacturer's instruction.

The results of the test are summarized in Table 7. At concentrations of 0.167% to 1.5%, both the whole fruit and peel serum fractions provided significantly more ARE activation than the control. The whole fruit also demonstrated a directional increase at 0.056% versus the control.

TABLE 7

ARE Activation

| v/v % Achachairu | Whole fruit[1] % increase vs control | p-value vs. control | Peel[2] % increase vs control | p-value vs. control |
|---|---|---|---|---|
| 1.5 | 929 | 0.000087 | 1133 | 0.000046 |
| 0.5 | 489 | 0.0023 | 614 | 0.00086 |
| 0.167 | 197 | 0.0076 | 209 | 0.0043 |
| 0.056 | 134 | .0.091 | 113 | 0.67 |
| 0.0185 | 103 | 0.96 | 92 | 0.79 |

TABLE 7-continued

ARE Activation

| v/v % Achachairu | Whole fruit[1] % increase vs control | p-value vs. control | Peel[2] % increase vs control | p-value vs. control |
|---|---|---|---|---|
| 0.006173 | 112 | 0.83 | 99 | 0.99 |
| 0.002058 | 93 | 0.89 | 92 | 0.94 |
| 0.000686 | 120 | 0.78 | 93 | 0.94 |

[1]Recentia ® GH from Ashland Specialty Ingredients
[2]Recentia ® GH-P from Ashland Specialty Ingredients Example 18

Melanin Synthesis Inhibition—B16 Assay

This example demonstrates the ability of Achachairu to inhibit the synthesis of melanin. Overproduction of melanin is generally associated with a variety of skin pigmentation conditions (e.g., age spots, vitiligo, solar lentigines, and melasma). Thus, without being limited by theory, it is believed that if Achachairu can demonstrate the ability to inhibit melanin production, then personal care compositions containing Achachairu may help improve the appearance of skin pigmentation conditions.

In this example, a commercially available B16-F1 mouse melanoma cell line from American Tissue Culture Collection, Va., USA was employed in a conventional melanin synthesis inhibition assay. The cell culture medium used in the assay is 500 mL of Dulbecco's Modified Eagle's Medium ("DMEM"), 50 mL Fetal Bovine Serum ("FBS"), and 5 mL of penicillin-streptomycin liquid. B16-F1 cells that are cultured in this medium and grown to greater than 90% confluency will synthesize melanin. While not intending to be bound by any theory, it is hypothesized that the melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., California, USA. Equipment used in the assay include a $CO_2$ incubator (e.g., a Forma Series Model 3110 by Therma Scientific, Massachusetts, USA or equivalent); a Hemocytometer (e.g., Bright Line model by Hauser Scientific, Pennsylvania, USA or equivalent); and a UV-Visible Spectrum Plate Reader (e.g., SpectraMax250 from Molecular Devices, California, USA or equivalent).

Day 0: To begin the assay, the cell culture medium is heated to 37° C. and 29 mL of the medium is placed into a T-150 flask. Approximately $1 \times 10^6$ of B16-F1 passage 1 mouse cells are added to the T-150 flask and incubated for 3 days at 37° C., 5% $CO_2$, 90% relative humidity, until ~80% confluency.

Day 3: The cells from the T-150 flask are trypsinized, and the number of cells is determined using the Hemocytometer. Initiate a 96 well plate with 2,500 cells per well in 100 μL of cell culture medium. Incubate the plate at 37° C., 5% $CO_2$, 90% relative humidity for 2 days until at least 20% to 40% confluent.

Day 5: Remove the cell culture medium from the plate and replace with fresh culture medium (100 uL per well). Add 1 uL of test compound diluted in a water solvent. Multiple dilution ratios may be tested in order to generate a dose response curve, wherein preferably three wells are treated with each dilution ratio. Positive and negative controls may include wells having the cell culture medium, B16-F1 cells, and the solvent (negative control), and wells comprising the cell culture medium, B16-F1 cells and a known melanin inhibitor (e.g., deoxyarbutin or kojic acid).

Day 7: Cells should have greater than ~90% confluency. If not, this data point is not used. Add 100 uL of a 0.75% sodium hydroxide solution to each well. Read the 96-well plate using the UV-Vis Plate Reader at 410 nm to optically measure the amount of melanin produced between wells that are treated with the fava bean extract and control wells that are not. Wells in which melanin is produced appear brownish in color. Wells in which little melanin is produced appear clear to light purple in color. Percentage of melanin synthesis inhibition is calculated by the following equation:

$$\frac{100 - [OD410 \text{ Test Compound} - OD410 \text{ Control \#2}] \times 100}{(OD410 \text{ Control \#1} - OD410 \text{ Control \#2})}$$

Where OD410 is the Optical Density at 410 nm as measured by the UV-Vis Spectrum Plate Reader.

When Control #3 is used, the formula for percentage melanin synthesis inhibition is:

$$\frac{100 - [OD410 \text{ Test Compound} - OD410 \text{ Control \#3}] \times 100}{(OD410 \text{ Control \#1} - OD410 \text{ Control \#2})}$$

The concentration of test agent needed to provide the IC 50 is recorded.

The results of the test are summarized in Table 2, which shows that Achachairu inhibits melanin synthesis, and thus is expected to provide a skin lightening benefit.

TABLE 8

Melanin Synthesis Inhibition B16 (IC 50)

| Composition | Concentration Needed for $IC_{50}$ (v/v %) |
|---|---|
| Achachairu[1] (whole fruit) | 0.19 |
| Achachairu[2] (peel only) | 0.19 |

[1]Recentia ® GH from Ashland Specialty Ingredients
[2]Recentia ® GH-P from Ashland Specialty Ingredients Example 19

Lipogenesis Inhibition

This example demonstrates the ability of Achachairu to inhibit lipogenesis in human pre-adipocytes. Lipogenesis involves the synthesis of commonly known lipids such as fatty acids and triglycerides, and is one of the primary ways mammals store energy. However, lipogenesis also involves the synthesis of lipids such as sebum. Sebum is a lipid produced by sebocytes, which are a type of skin cell found primarily in the sebaceous glands of mammalian skin. Sebum is produced by the body to lubricate and waterproof the skin and hair of mammals. However, overproduction of sebum can result in oily appearing skin and/or skin that appears to have poor texture. Thus, without being limited by theory, it is believed that if Achachairu can demonstrate the ability to inhibit lipogenesis, then personal care compositions containing Achachairu may help regulate conditions of mammalian keratinous tissue associated with sebum overproduction.

Method:

Human pre-adipocytes were selected for use in this example. Because of the known difficulty associated with culturing and testing sebocytes, pre-adipocytes are commonly used as a surrogate for sebocytes to determine the potential of a test agent to inhibit sebum production.

Human subcutaneous pre-adipocytes purchased from Zen-Bio, Inc. (Cat. # SP-F-SL) were cultured in PM-1 media (available from Zen-Bio, Inc as Cat# PM-1 (plus 5 ng/ml EGF)) to 80-90% confluency. The cells were transferred to 96-well clear bottom white plates to provide approximately 40,625 cells/cm$^2$ in the well (approx. 12,500 cells) and 150 µl of PM-1 media per well, and then cultured for 24-48 hours in a 5% $CO_2$ incubator at 37° C. The PM-1 media was then replaced with differentiation medium (Zen-Bio, Inc. Cat# DM-1), and the cells were incubated for another 6 days. After incubating in the differentiation medium, 90 µl of the differentiation medium was carefully replaced with 140 µl of human subcutaneous adipocyte medium ((Zen-Bio, Inc. Cat# AM-1). Care was taken not to touch or disturb the cells at the bottom of the well. 2 µl of Achachairu ingredient (Recentia® GH-P from Ashland Specialty Ingredients) or control composition (100 µM Genistein (Cat# G6649) from Sigma) was added to each well daily for 9 days (total incubation of 15 days). On Day 15, 5 µL of AdipoRed reagent (Lonza; Cat. Number: PT-7009) was slowly added directly to cells in the treatment medium, and the plate was gently mixed after each row addition. The plate was incubated for 15 minutes at room temperature. Lipogenesis was quantitated using an EnVision® brand Fluorescent spectrophotometer Plate Reader according to the AdipoRed protocol. The plates were scanned from the bottom using the 451 mirror and (excitation 485 nm; emission 535) filters. Each well was scanned in a Z pattern (7 reads across from left to right, 7 reads diagonally from right to left and 7 reads across from left to right for a total of 21 end points).

Percent Inhibition was Calculated as $$\frac{\text{Average Control } RFU - \text{Sample } RFU}{\text{Average Control } RFU} \times 100$$

The cells were assayed and normalized to the control by using a FluoReporter® Blue Fluorometric brand dsDNA Quantitation Kit. Immediately after the screen the AdipoRed containing cell media was gently aspirated, cells were rinsed with 100 ul 1×PBS taking care not to dislodge them from the bottom and 100 µl distilled water was added/well. The plates were frozen at −80° C. to lyse the cells and assayed according to the kit instructions at a later date.

The results of the test are summarized in Table 3, which shows that Achachairu ingredient inhibits lipogenesis, and thus is expected to help regulate conditions associated with the overproduction of sebum.

TABLE 9

Lipogenesis Inhibition

| Composition | IC 50 w/v % |
|---|---|
| Recentia ® GH-P (Achachairu Peel) | 0.4% |
| Recentia ® GH (Achachairu Whole Fruit) | 0.5% |

Example 20

Inhibiting the Cell's Inflammation Response to a Stressor-NF-Kappa-Beta ("NF-kB") Assay This example demonstrates the ability of Achachairu ingredients to inhibit NF-kB activation. NF-kB (i.e., nuclear factor kappa-light-chain-enhancer of activated B cells) is a protein complex that belongs to the category of "rapid-acting" primary transcription factors (i.e., transcription factors that are present in cells in an inactive state and do not require new protein synthesis in order to become activated), which allows NF-kB to be a first responder to harmful cellular stimuli such as ROS and other stressors. NF-kB is found in almost all animal cell types and is known to be involved in the cellular inflammation pathway. Cellular inflammation is associated with a variety of skin conditions, and thus inhibiting NF-kB activation vis-à-vis cellular inflammation may help treat these types of skin conditions.

Method:

CellSensor™ NF-κB-bla HEK 293T cells (Invitrogen, Cat. # K1165) were plated in assay medium (DMEM with high glucose (Gibco, Cat. #11965) plus 10% dialyzed FBS). The cells were cultured and seeded at 10,000/well in 96-well plates (black-sided Poly-D-Lysine coated plates, BD #356692), and then incubated at 37° C. and 95% RH for the 72 hours prior to testing. Recombinant human TNFα (available from R&D systems) was used to stimulate NF-kB activation in the cells. Fisetin (3, 7, 3', 4'-tetrahydroxyflavone) was used to inhibit stimulation of the cells by TNFα. A ToxBLAzer™ DualScreen brand screening kit (Invitrogen, Cat. #K1138) was used as the fluorescent substrate according to the manufacturer's instructions.

The following controls were run on each plate in the assay:

High control (Stimulated)=cells+TNFα+1% DMSO
Blank (Unstimulated)=cells+1% DMSO
Standard (Positive control inhibitor)=cells+TNFα+Fisetin+1% DMSO
Negative Control (no cells)=assay medium NF-κB % Inhibition is Calculated as $$\frac{\text{High Control} - \text{Sample}}{\text{High Control} - \text{Blank}} \times 100$$

The results of this test are summarized in Table 10 below. As illustrated in Table 10, the Achachairu whole fruit serum fractions and Achachairu peel serum fractions provided an IC 50 for NF-kB inhibition of 2%. Thus, a personal care composition comprising Achachairu ingredients may be useful for regulating a condition of mammalian keratinous tissue related to cellular inflammation.

TABLE 10

| Composition | $IC_{50}$ (v/v %) | Cytotoxicity |
|---|---|---|
| Recentia ® GH-P (from Achachairu Fruit Peel only) | 2% | None observed |
| Recentia ® GH (from Achachairu Whole Fruit) | 2% | None observed |

Example 21

Inhibiting the Cell's Inflammation Response to a Stressor—Prostaglandin E2 ("PGE2") Assay This example demonstrates the ability of Achachairu ingredients to inhibit PGE2 activation. PGE2 is a hormone-like substance that is known to participate in modulation of inflammation, Cellular inflammation is associated with a variety of skin conditions, and thus inhibiting PGE2 activation vis-à-vis cellular inflammation may help treat these types of skin conditions.

Method

Tert keratinocytes ("tKC") were plated at 40,000 cells/well into 24-well plates in 1 ml/well volume. EpiLife Medium (Life Technologies cat # MEPICFPRF500) supplemented with keratinocyte growth supplement (Life technologies cat #S-001-5) was used as the assay media. The cells were grown to confluence/near confluence, and then subjected to 15 $mJ/cm^2$ UVB-stress. The test compositions (Achachairu and vehicle control) (diluted 1:1000) were added, and the plates were incubated for 18-24 hours. The supernatant was removed from each well, and the cells were rinsed with 2 ml/well medium (without supplements). A Cell Titer-Glo assay (measures ATP activity) was conducted on the cells for normalization. The supernatant was tested in a PGE2 assay (Prostaglandin E2 Assay kit from Cisbio Bioassays cat#62P2APEB) according to the manufacturer's instructions. The PGE2 results were normalized to ATP activity.

The results of the PGE2 assay are summarized in Table 11. The Achachairu Whole Fruit serum fraction and Achachairu Peel serum fractions both demonstrated the ability to inhibit release of PGE2 from keratinocytes exposed to 15 mJ/cm2 UVB radiation, which illustrates anti-inflammatory activity of Achachairu ingredients. Thus, a personal care composition comprising Achachairu ingredients may be useful for regulating a condition of mammalian keratinous tissue related to cellular inflammation.

TABLE 11

| Test | PGE2 Release (% of vehicle control) | StDev |
|---|---|---|
| Recentia ® GH-P (from Achachairu Fruit Peel) | 28% | 8.20% |
| Recentia ® GH (from Achachairu Whole Fruit) | 52% | 11.40% |
| Vehicle control | 98% | 13.20% |

Example 22

Protein Loss Inhibition

This example demonstrates the ability of Achachairu ingredients to inhibit protein loss in hair. Hair is a protein filament formed primarily of keratin that grows from follicles found in the dermis of mammalian skin. The proteins (i.e., keratin) in hair can be damaged by a variety of endogenous and exogenous stressors (e.g., UV radiation), which can lead to, e.g., dry, brittle, and/or dull looking hair. Thus, it would be desirable to inhibit, prevent or even reverse undesirable protein loss in hair.

It is believed, without being limited by theory, that changes in the level of certain amino acids found in keratin correspond to the overall change in protein level in hair. In this test, serine, proline, glutamic acid, and valine were used as surrogates for overall protein level, since these amino acid residues represent approximately 40% of the protein concentration.

Method

Achachairu whole fruit serum fraction (Recentia® GH) was formulated at 2% (w/v) in a 50:50 ethanol:water chassis with 2% SEPIMAX ZEN brand thickener (Seppic, France) to a final pH of 6.0 to provide a test composition. The same composition, except without any Achachairu serum fraction, was used as a control. The test composition and control composition were applied to light-brown, non-chemically-treated, 2 g, flat hair switches (6 switches per leg) at 0.2 g/g, and thoroughly distributed through-out the hair switch. Twenty-four hours after treatment, the switches were washed with Pantene® Volume brand shampoo (from the Procter & Gamble Co.). This treatment/wash cycle was repeated ten times, but the hair switches were not washed after the tenth treatment. After the tenth treatment, half the switches from the control and test group were tested for protein loss (0 hours), and the other half were exposed to 40 hours of ultraviolet radiation in an Atlas™ Ci3000+ brand weather-o-meter and then tested for protein loss (40 hours). An internal and outer quartz filter was used to simulate broad-spectrum, outdoor daylight with a specific irradiance of 1.48 $W/m^2$ at 420 nm. Temperature and relative humidity were kept constant at 35° C. and 80% RH. After the UV exposure, the hair switches were tested for protein loss.

Protein levels are determined using the following method. 0.2-0.3 g hair samples (2 inches length) are collected from each hair switch and are added to glass scintillation vials. Distilled water is added at a ratio of 10:1 (mL water to g hair). Samples are shaken for 1 h at 2500 rpm on a DVX-2500 Multi-tube Vortexer platform. Amino acid concentration is determined after acid hydrolysis using High-Performance Liquid Chromatography/Mass Spectrometry (HPLC/MS/MS). The analytes (Serine, Proline, Valine, Glutamic acid) and their corresponding internal standards are subjected to hydrophilic interaction chromatography (HILIC) analysis on a ZIC-HILIC column (2.1×150 mm, 5 micron particles). Detection and quantitation is by tandem mass spectrometry operating under multiple reaction monitoring (MRM) MS/MS conditions. The amino acid concentrations are determined by back-calculation using a weighted quadratic regression of a calibration curve generated from neat standards.

The results of the test are summarized in Table 12 and illustrated in FIGS. 5-9. Amino acid levels are shown in μg/g. P-values of 0.1 or less are considered statistically significant. P-values of greater than 0.1 but less than 0.2 are considered directional. As indicated in Table 12 and FIGS. 5-9, the amount of amino acid loss observed when the samples were exposed to UV radiation for 40 hours increased relative to the corresponding 0 hour samples. However, the Achachairu-treated samples exhibited less protein loss at 0 hours and after 40 hours of UV exposure compared to their respective non-Achachairu treated counterparts. In addition, the samples treated with Achachairu ingredients did not exhibit a statistically significant difference in protein loss after 40 hours of UV exposure when compared to the untreated samples at 0 hours. Thus, treatment with the Achachairu serum fraction appears to reduce UV-induced protein loss, and the reduction in protein loss at 0 hours suggests that treatment with Achachairu ingredients may also reduce protein loss in hair due to non-UV stressors.

TABLE 12

|  | Serine | Glutamine | Valine | Proline | Total |
|---|---|---|---|---|---|
| (a) 0 hours Control | 32.00 | 24.58 | 8.50 | 14.48 | 79.54 |
| (b) 0 hours treated w/ Achachairu | 26.61 | 20.75 | 7.26 | 12.91 | 67.49 |
| (c) 40 hours Control | 41.87 | 35.05 | 12.82 | 21.03 | 110.79 |
| (d) 40 hours treated w/ Achachairu | 31.38 | 25.26 | 8.90 | 14.95 | 80.48 |
| $\Delta_{a\text{-}b}{}^1$ | 5.39 | 3.83 | 1.24 | 1.67 | 12.05 |
| p-value | 0.049 | 0.0646 | 0.1453 | 0.2165 | 0.0755 |
| $\Delta_{a\text{-}c}{}^2$ | 9.87 | 10.57 | 4.32 | 6.45 | 31.25 |
| p-value | 0.0007 | <0.0001 | <0.0001 | 0.0001 | <0.0001 |
| $\Delta_{a\text{-}d}{}^3$ | 0.62 | 0.78 | 0.40 | 0.37 | 0.94 |
| p-value | 0.8190 | 0.6920 | 0.6412 | 0.7824 | 0.8899 |
| $\Delta_{b\text{-}d}{}^4$ | 4.77 | 4.51 | 1.64 | 2.04 | 12.99 |
| p-value | 0.062 | 0,0197 | 0.0446 | 0.1119 | 0.0442 |

[1]Difference between Control level at 0 hours and Treated level at 0 hours.
[2]Difference between Control level at 0 hours and Control level at 40 hours.
[3]Difference between Control level at 0 hours and Treated level at 40 hours
[4]Difference between Treated level at 40 hours and Treated level at 0 hours.

Example 23

Preservative System for the Achachairu (*Garcinia humilis*) Fractions and Extracts Various preservatives and stabilizers were tested for use with the bioactive serum fractions and bioactive extracts of the present invention.

Provided below in Table 13 is one example of a combination/concentrations of preservatives and stabilizers that was used for preparing finished ingredients (e.g., those described in Examples 1, 2, and 3), as follows:

TABLE 13

| Preservative/Stabilizer | Amount (wt %) |
|---|---|
| Pentylene Glycol (CAS 5343-92-0) | 1.90% |
| Tetrasodium EDTA (CAS 64-02-8) | 0.25% |
| Sodium metabisulfite (CAS 7681-57-4) | 0.20% |
| Potassium sorbate (CAS 590-00-1) | 0.10% |
| Sodium Benzoate (CAS 532-32-1) | 0.10% |
| Bioactive Serum Fraction or Extract | 97.45% |

While the preservatives and stabilizers provided above were found to be effective, other preservatives and stabilizers that are known in the art could also be as affective with the bioactive serum fractions and bioactive extracts of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

As used in the description and the appended claims, the singular forms "a," "an," and "the" are intended to include the plural forms as well, unless the context clearly indicates otherwise. All percentages disclosed herein are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. All numeric ranges are inclusive of narrower ranges and combinable; delineated upper and lower range limits are interchangeable to create further ranges not explicitly delineated.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bioactive serum fraction derived from an Achachairu (*Garcinia humilis*) plant wherein said bioactive serum fraction comprises: (i) a total benzophenone content of less than 0.10 wt %, wherein said benzophenone is Guttiferone A and, (ii) a total protein content of less than 0.15 wt %, wherein the bioactive serum fraction comprises bioactive properties selected from the group consisting of anti-oxidant activity, anti-inflammatory activity, anti-aging activity and anti-irritant activity.

2. The bioactive serum fraction according to claim 1, wherein said serum fraction is isolated from a whole fruit, a particular part of the whole fruit, or a leaf of said Achachairu (*Garcinia humilis*) plant, or any combination thereof.

3. The bioactive serum fraction according to claim 2, wherein said particular pan of the whole fruit is selected from the group consisting of a peel part, a flesh part, and a seed part.

4. A bioactive extract derived from an Achachairu (*Garcinia humilis*) plant wherein said bioactive extract comprises a total benzophenone content of less than 0.10 wt %, wherein said benzophenone is Guttiferone A and a total protein content of less than 0.15 wt wherein the bioactive extract comprises bioactive properties selected from the group consisting of anti-oxidant activity, anti-inflammatory activity, anti-aging activity and anti-irritant activity.

* * * * *